(12) United States Patent
Thompson et al.

(10) Patent No.: US 7,011,795 B2
(45) Date of Patent: Mar. 14, 2006

(54) APPARATUS FOR DISPERSING SCENTS INTO THE ENVIRONMENT

(75) Inventors: Stanley O. Thompson, New Boston, NH (US); Ricardo Silveira, Bridgewater, MA (US); David Bossa, Uxbridge, MA (US); Jaideep Jayaram, Milford, MA (US); Brice Daniel Westring, Mason, OH (US); Keith Fanta, Liberty Township, OH (US); Stephan Gary Bush, Hamilton, OH (US); Bruce Chang, Tai-Chung (TW)

(73) Assignees: JCS/THG, LLC, Milford, MA (US); The Procter & Gamble Company, Cincinnati, OH (US)

( * ) Notice: Subject to any disclaimer, the term of this patent is extended or adjusted under 35 U.S.C. 154(b) by 94 days.

(21) Appl. No.: 10/449,918

(22) Filed: May 29, 2003

(65) Prior Publication Data

US 2004/0241053 A1    Dec. 2, 2004

(51) Int. Cl.
*A62B 7/08* (2006.01)
*B23B 29/24* (2006.01)

(52) U.S. Cl. .................. 422/125; 74/813 R; 74/815; 74/816; 222/167; 261/30; 261/DIG. 65; 422/123

(58) Field of Classification Search .......... 422/125, 422/4, 5, 105, 116, 122, 123; 261/30, DIG. 65; 222/167; 74/813 R, 815, 816
See application file for complete search history.

(56) References Cited

U.S. PATENT DOCUMENTS

| | | | |
|---|---|---|---|
| 2,103,609 A | 12/1937 | Bradburn | |
| 2,555,047 A | 5/1951 | Logue | |
| 2,608,436 A | 8/1952 | Baughman | |
| 3,410,488 A | 11/1968 | Sugimura | |
| 3,711,023 A | 1/1973 | Smith | |
| 3,908,905 A | 9/1975 | Von Phlipp et al. | |
| 4,064,203 A | 12/1977 | Cox | |
| 4,094,639 A | 6/1978 | Mcmillan | |
| 4,301,095 A | 11/1981 | Mettler et al. | |
| 4,361,427 A | 11/1982 | Barradas | |
| 4,549,250 A | 10/1985 | Spector | |
| 4,570,824 A | 2/1986 | Bolling | |
| 4,603,030 A | 7/1986 | Mccarthy | |
| 4,629,604 A | 12/1986 | Spector | |

(Continued)

FOREIGN PATENT DOCUMENTS

CA         2222838         1/1997

(Continued)

*Primary Examiner*—Krisanne Jastrzab
(74) *Attorney, Agent, or Firm*—Hoffman & Baron, LLP; Francis E. Marino

(57) ABSTRACT

The present invention is a device for playing a cartridge for dispersing scented materials into a room. The cartridge generally has a plurality of scent elements supported on a rotatable disk. The device includes a housing, a blower assembly, a platter, a motor, first and second sensors and a control unit. The housing has a cavity for receiving the cartridge and is formed with an air intake and an exhaust port. The blower assembly is mounted within the housing for generating an airflow by drawing air in through the air intake over the cavity to diffuse at least one of the plurality of scent elements out through the exhaust port. The platter is configured to engage the rotatable disk and is rotated by the motor. The platter, first and second sensors and a control unit cooperate to control the rotation of the disk. The device can also include a heating element for activating the scent elements.

24 Claims, 34 Drawing Sheets

U.S. PATENT DOCUMENTS

| | | |
|---|---|---|
| 4,695,434 A | 9/1987 | Spector |
| 4,714,984 A | 12/1987 | Spector |
| 4,743,406 A | 5/1988 | Steiner et al. |
| 4,808,347 A | 2/1989 | Dawn |
| 4,865,816 A | 9/1989 | Walz et al. |
| 4,921,636 A | 5/1990 | Traas |
| 5,023,020 A | 6/1991 | Machida et al. |
| 5,034,222 A | 7/1991 | Kellett et al. |
| 5,071,621 A | 12/1991 | Tokuhiro et al. |
| 5,163,616 A | 11/1992 | Bernarducci |
| 5,167,877 A | 12/1992 | Pai |
| 5,178,327 A | 1/1993 | Palamand et al. |
| 5,220,636 A | 6/1993 | Chang |
| 5,234,162 A | 8/1993 | Sullivan |
| 5,269,723 A | 12/1993 | Bender |
| 5,342,584 A | 8/1994 | Fritz et al. |
| 5,345,617 A | 9/1994 | Jahner et al. |
| 5,407,642 A | 4/1995 | Lord |
| 5,478,505 A | 12/1995 | McElfresh et al. |
| 5,498,397 A | 3/1996 | Horng |
| 5,527,493 A | 6/1996 | McElfresh et al. |
| 5,565,148 A | 10/1996 | Pendergrass, Jr. |
| 5,624,230 A | 4/1997 | Taylor et al. |
| 5,658,387 A * | 8/1997 | Reardon et al. ............ 118/323 |
| 5,662,835 A | 9/1997 | Collingwood |
| 5,732,882 A | 3/1998 | Gibbs |
| 5,735,918 A | 4/1998 | Barradas |
| 5,752,658 A | 5/1998 | Gibbs et al. |
| 5,805,768 A | 9/1998 | Schwartz et al. |
| 5,887,118 A | 3/1999 | Huffman et al. |
| 5,899,382 A | 5/1999 | Hayes et al. |
| 5,932,147 A | 8/1999 | Chen |
| 5,935,526 A | 8/1999 | Moore |
| 5,972,290 A | 10/1999 | DeSousa |
| 6,013,524 A | 1/2000 | Friars et al. |
| 6,024,783 A | 2/2000 | Budman |
| 6,029,900 A | 2/2000 | Quinones |
| 6,060,045 A | 5/2000 | Mettler |
| 6,083,456 A | 7/2000 | Van Rees |
| 6,099,137 A | 8/2000 | McCormack et al. |
| 6,103,201 A | 8/2000 | Green |
| 6,136,277 A | 10/2000 | Nardini |
| 6,152,829 A | 11/2000 | Jaidka |
| 6,179,219 B1 | 1/2001 | Lin |
| 6,197,263 B1 | 3/2001 | Blount |
| 6,254,823 B1 | 7/2001 | Rees |
| 6,270,720 B1 | 8/2001 | Mandish |
| 6,315,959 B1 | 11/2001 | Mandish |
| D459,950 S | 7/2002 | Bush et al. |
| 6,435,419 B1 | 8/2002 | Davis |
| D463,437 S | 9/2002 | Bush et al. |
| 6,514,467 B1 | 2/2003 | Bulsink et al. |
| 6,602,475 B1 * | 8/2003 | Chiao ........................ 422/124 |
| 2001/0048641 A1 | 12/2001 | Kaston |
| 2002/0048530 A1 | 4/2002 | Wohrle |
| 2002/0066798 A1 | 6/2002 | Laudamiei-Pellet |
| 2002/0066967 A1 | 6/2002 | Bartsch et al. |
| 2002/0068009 A1 | 6/2002 | Laudamici-Pellet |
| 2002/0068010 A1 | 6/2002 | Laudamici-Pellet |

FOREIGN PATENT DOCUMENTS

| | | |
|---|---|---|
| DE | DES. 252706 | 8/1979 |
| EP | 0 295 129 | 12/1988 |
| WO | WO 97/02076 | 1/1997 |
| WO | WO 99/08174 | 2/1999 |
| WO | WO 00/12143 | 3/2000 |
| WO | WO 01/19417 A1 | 3/2001 |
| WO | WO 02/09772 A2 | 2/2002 |

* cited by examiner

FIG. 22
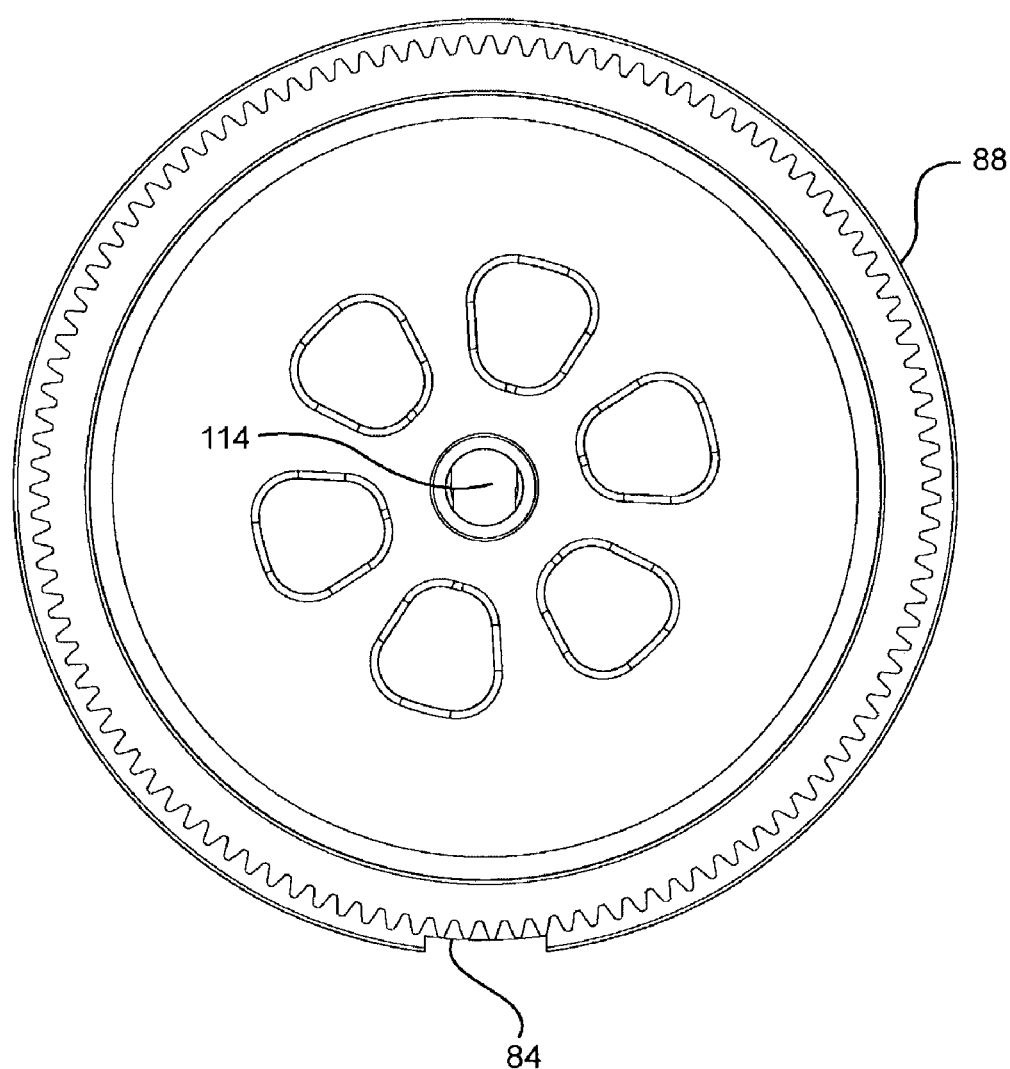
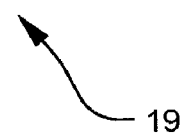

APPARATUS FOR DISPERSING SCENTS INTO THE ENVIRONMENT

BACKGROUND OF THE INVENTION

1. Field of the Invention

The present invention relates generally to a method and apparatus for dispersing volatile materials into the environment. In particular, the present invention is directed to a device that disperses a plurality of different scents into the air. The present invention is also directed to a device for rotating an object a predetermined range about an axis.

2. Brief Description of the Prior Art

PCT Publication WO 02/09772 discloses a device for dispensing a plurality of scents into the air. The device 20 employs a replaceable cartridge 22. The cartridge can include a plurality of different scent elements. The cartridge 22 is designed so that all of the scent elements are sealed when the cartridge is removed from the device 20. The plurality of scent elements can be supported on a circular rotatable disk 46 formed with a plurality of pockets 44. The pockets 44 are arranged to have a blank space located between at least two of the pockets 44. The plurality of scent elements are preferably in the form of a gel, but can include: solids, liquids, beads, encapsulates, wicks, carrier materials, and combinations thereof. The plurality of scent elements can be related to an overall "theme" or "physiological effect." For example, the plurality of scent elements can all be fruit scents.

The device 20 disclosed in PCT Publication WO 02/09772 generally includes a component for activating the scent elements and a component for diffusing the aromatic materials. The component for activating the scent elements can be one or more heating elements 132. The component for diffusing the aromatic materials can be a fan 134. The device can include a mechanism for aligning the heater 132 with one or more scent elements, or the device can be configured to include a heating element located under each pocket 44. The device 20 includes a motor 142 and a pair of gears 144, 146 for rotating the disk 46 within the cartridge 22. The gears include a worm gear 146 and a plate gear 144 that are configured to rotate a shaft 138 that engages the disk 46. The device 20 includes electronic controls which can be configured to allow the user to: start and stop the device; control the volume and intensity of the scent; and control the selection of the scent including skipping a scent that is included in the cartridge 22.

PCT Publication No. WO 00/12143 discloses an odor dispensing device and cartridge. The device includes a housing and a disc shaped cartridge. The cartridge is adapted to move around its rotation axis and includes a plurality of radially arranged compartments which contain an odorant carrier. The device includes a fan 21 for producing an airstream which is directed to a selected compartment. The cartridge is rotated by a drive belt 38 and can include a number of scents. The device is configured to position the cartridge and produce an airstream to the selected compartment in response to a signal from: a computer control module; a microprocessor; an optical system; or a timing mechanism.

U.S. Pat. No. 5,805,768 to Schwartz, et al. discloses an apparatus for diffusing aroma therapy oils which allow the user to pre-select a variety of aromas to be introduced at predetermined time intervals so that different moods or state of minds can be created. The apparatus includes a tray having a plurality of receptacles for various aromatic materials, and a heating means for heating a pre-selected receptacle, and thus aromatic material. The apparatus also includes a motor driven timer, that rotates the tray, so that the plurality of receptacles containing different aromatic materials are exposed to the heating means at a predetermined time period. The apparatus further includes a lid with a hole that exposes the pre-selected receptacle and aromatic material when the receptacle and aromatic material are exposed to the heating means. The aroma released from the heated aromatic material emanates into the environment through the hole. The remaining receptacles, which are out of close proximity to the heating means, are sealed to avoid the evaporation of the aromatic materials.

U.S. Pat. No. 5,565,148 to Pendergrass, Jr. discloses an apparatus for delivering one or more aromas at selected times. The apparatus includes a housing with a receptacle and an aroma delivery device detachably received in the receptacle. The aroma delivery device includes a carrier having a plurality of aroma-bearing elements that are selectively communicated with an air passageway for providing one or more aromas as desired. The device is especially useful for providing a realistic sensory experience in an interactive or non-interactive use, and may be used in such diverse settings as the entertainment industry, the educational training field or a medical arena.

U.S. Pat. No. 5,178,327 to Palamand, et al. discloses an air freshener that includes a container which carries a cartridge having a plurality of sections, each of which is filled with a porous material impregnated with a differently scented substance. At least the front wall of the container has an aperture of generally the same shape and size as the cartridge sections. The cartridge may be rotated within the container to selectively bring one of its sections into alignment with the aperture, in order to expose a scented substance in one of the sections to the ambient air contained within a room, causing evaporation of the scented substance and freshening of the room's air. The back wall of the container may also be provided with an aperture, which is in general axial alignment with the front wall aperture, and tape or the like surrounding the aperture, so that the air freshener may be mounted over a vent or the like. In this manner, the fragrant scent will be spread into a room by force rather than by convection.

U.S. Pat. No. 4,629,604 to Spector discloses a player for a multi-aroma cartridge constituted by a planar array of like frame assemblies held within a multi-section framework, each assembly being formed by a pad of absorbent material sandwiched between a pair of frames whose margins are joined together to define a central zone exposing the pad. The pad of each assembly is impregnated with a liquid fragrance that differs from those of the others. When the cartridge is inserted in a slot in the player case, it lies over a complementary honeycomb, each of whose cells is then in registration with a respective assembly. The cells are provided with individual electric heaters such that when a selected cell heater is energized, it heats the air in the cell to produce a positive pressure therein that acts to force the heated air through the zone to volatilize the liquid fragrance, the resultant aromatic vapor being discharged into the atmosphere through vents in the case. The selection of aromas to be played may be effected manually or it may be synchronized to follow the scenes of a video tape or movie film presentation.

U.S. Pat. No. 4,603,030 to McCarthy discloses a system for emitting, in sequence, a plurality of different scents. The system includes a plurality of holders for scent-bearing chips; a mechanism for propelling these scents from the system; a mechanism for selectively conveying any desired scent holder into operative relation with the propelling mechanism; and a mechanism for actuating the propelling mechanism to propel scent from any desired scent holder in response to a programmed, predetermined sequence of scents of predetermined duration.

SUMMARY OF THE INVENTION

The present invention is a device for playing a cartridge for dispersing scented materials into a room. The cartridge generally has a plurality of scent elements supported on a rotatable disk. The device includes a housing, a blower assembly, a platter, a motor, first and second sensors and a control unit. The housing has a cavity for receiving the cartridge and is formed with an air intake and an exhaust port. The blower assembly is mounted within the housing for generating an airflow by drawing air in through the air intake over the cavity to diffuse at least one of the plurality of scent elements out through the exhaust port. The platter has a body defined by a perimeter and a center, a hub, and first and second position indicators. The hub is configured to removably engage the rotatable disk of the cartridge and is connected to the body at the center to define an axis of rotation. The first and second position indicators are connected to the body. The motor is mounted within the housing and coupled to the platter for rotating the platter about the axis of rotation so that the first position indicator rotates through a first circular path and the second position indicator rotates through a second circular path. The first sensor is arranged adjacent to a first point on the first circular path and generates a first signal when the first position indicator is rotated to the first point. The second sensor is arranged adjacent to a second point on the second circular path and generates a second signal when the second position indicator is rotated to the second point. The control unit is electrically coupled to: the first sensor; the second sensor; and the motor, and controls the current delivered to the motor to operate the motor. The control unit alters the current delivered to the motor upon receiving either the first signal from the first sensor or the second signal from the second sensor. The device also preferably includes a heating element positioned within the cavity for activating at least one of the plurality of scent elements.

In preferred embodiments of the invention, the first position indicator is a first tubular ring formed with at least one notch which is positioned to correspond with a home position of the rotatable disk of the cartridge. The second position indicator is a second tubular ring formed with a plurality of notches. Each notch is positioned to correspond with a location of one of the plurality of scent elements on the rotatable disk of the cartridge. The first and second sensors are preferably optical sensors configured to detect the location of the notches corresponding to the home position and location of the scent elements on the rotatable disk of the cartridge. The optical sensors are preferably formed with a slot so that an edge of each respective tubular ring can ride within the slot. The device preferably includes a cover and a latch configured to cooperate to cover the cavity. The cover is rotatably connected to the housing and the latch is configured to maintain the cover in the closed position and is formed with a key. Preferably the perimeter of the platter is formed with a latch notch that corresponds to the home position of the rotatable disk. The latch notch is configured to receive the key so that the latch can be translated to open the cover when the platter is at the home position. The motor is preferably configured to be operated under direct current and is coupled to the platter through a plurality of gears to increase the torque delivered to the platter. The motor preferably includes a first terminal maintained at a ground potential and a second terminal maintained at a high potential during the operation of the motor. The control unit is preferably configured to alter the current delivered to the motor by at least one of:
 isolating one of the first and second terminals to stop the current flowing through the motor;
 providing an alternate path in parallel with the second terminal to divert current from flowing through the motor; and
 applying a substantially high potential to the first terminal.

During the operation of the device, the control unit is preferably configured to sequentially rotate the hub from the home location through each location of a scent element and back to the home location. The control unit is preferably configured to stop the rotation of the hub for a play period at each of the plurality of scent elements. When a heating element is included in the device, the control unit is preferably configured to operate the heating element during at least a portion of the play period.

BRIEF DESCRIPTION OF THE DRAWINGS

Preferred embodiments of the invention have been chosen for purposes of illustration and description and are shown in the accompanying drawings, wherein:

FIG. 22 is a bottom plan view of the platter;

DETAILED DESCRIPTION OF THE INVENTION

Figure 1:
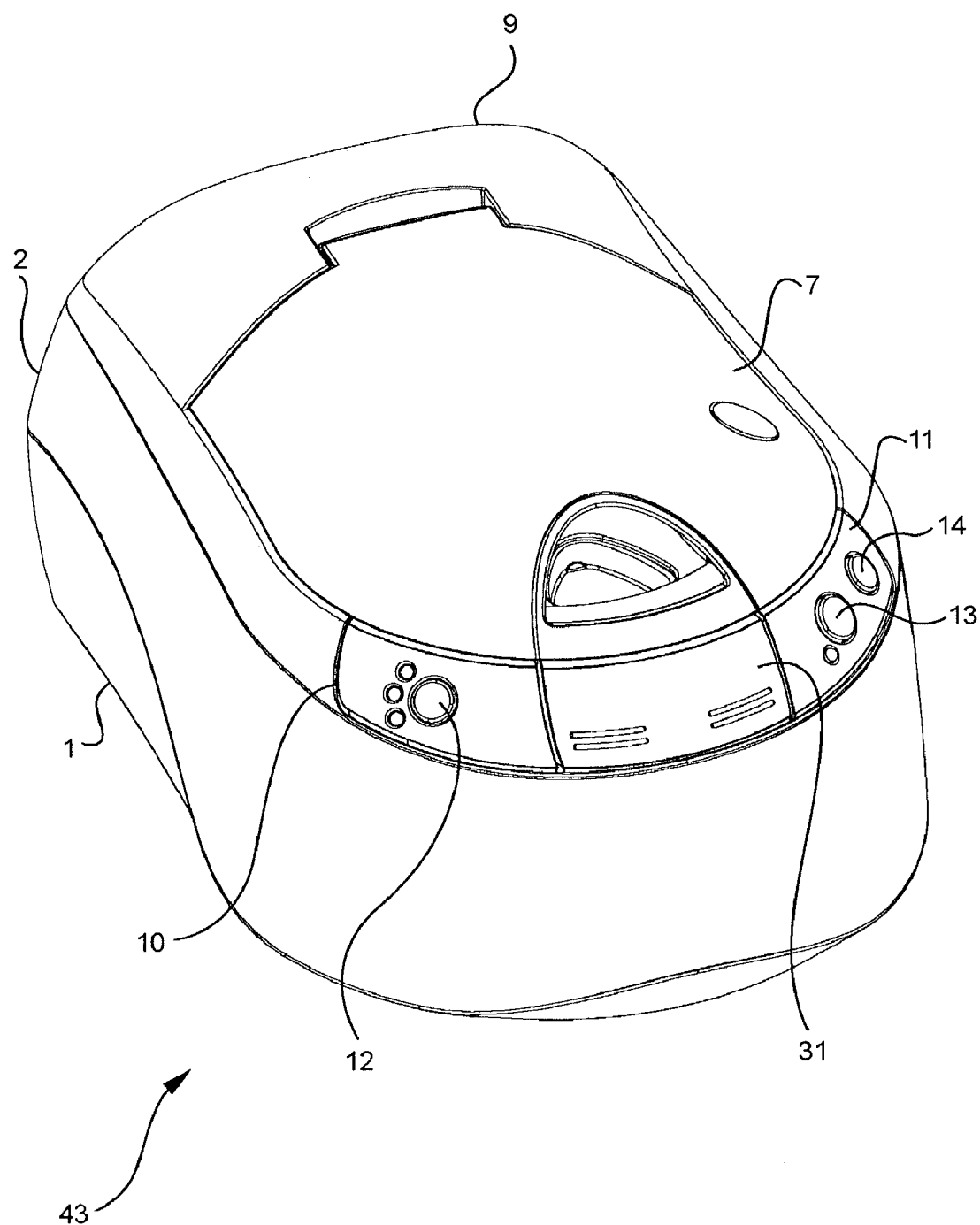
FIG. 1 is a perspective view of the present invention.

Referring initially to FIGS. 1 through 11, the device 43 for dispensing volatile materials into the environment is configured to play a replaceable cartridge 42 that includes a plurality of different scent elements. The cartridge 42 is preferably designed so that all of the scent elements are sealed when the cartridge is removed from the device 43. The plurality of scent elements are generally supported on a rotatable disk formed with a plurality of pockets. The pockets are preferably arranged to have a blank space located between at least two of the pockets that defines a home position. The plurality of scent elements are preferably in the form of a gel, but can include: solids, liquids, beads, encapsulates, wicks, carrier materials, and combinations thereof. The scent elements preferably require some form of activation to prevent the scent element from prematurely volatizing on its own.

The device generally plays the cartridge 42 by initially selecting and positioning one of the plurality of scent elements for diffusion. When the scent element is in the preferred form that requires activation, such as a gel, the scent element is next activated. The activated scent element is then diffused into the environment. In order to accomplish these steps in playing the cartridge 42, the device 43 generally includes a drive assembly 66, a heating assembly 68, a blower assembly 70, and a positioning assembly 72 contained within a housing. The device 43 also includes a control unit 73 that controls and coordinates the operation of the individual assemblies.

The cartridge 42 that is played by the device 43 is disclosed in a U.S. Patent Application Publication No. 2004/0016818. entitled "Volatile Material-Containing Article" by Rachel Murdell and Stephan G. Bush filed on May 29, 2003, which is incorporated herein by reference. In order to play the cartridge 42, the drive assembly 66 generally needs to generate a torque of about 5 inch pounds to rotate the disk within the cartridge 43 for positioning the scent elements. The blower assembly 70 preferably delivers an airflow at a constant velocity of about 800 feet per minute, and the heating assembly 68 preferably is configured to be heated to a temperature in a range from about 60 to about 120 degrees Celsius.

Referring to FIGS. 1 through 6, the device 43 includes a housing that contains the drive assembly 66, the heating assembly 68, the blower assembly 70, the positioning assembly 72, and the control unit 73 which are described in detail below. The housing generally includes a bottom housing 1, a top housing 2, a top cover 7, and a top cap 9, and is preferably made from a plastic.

Figure 9:
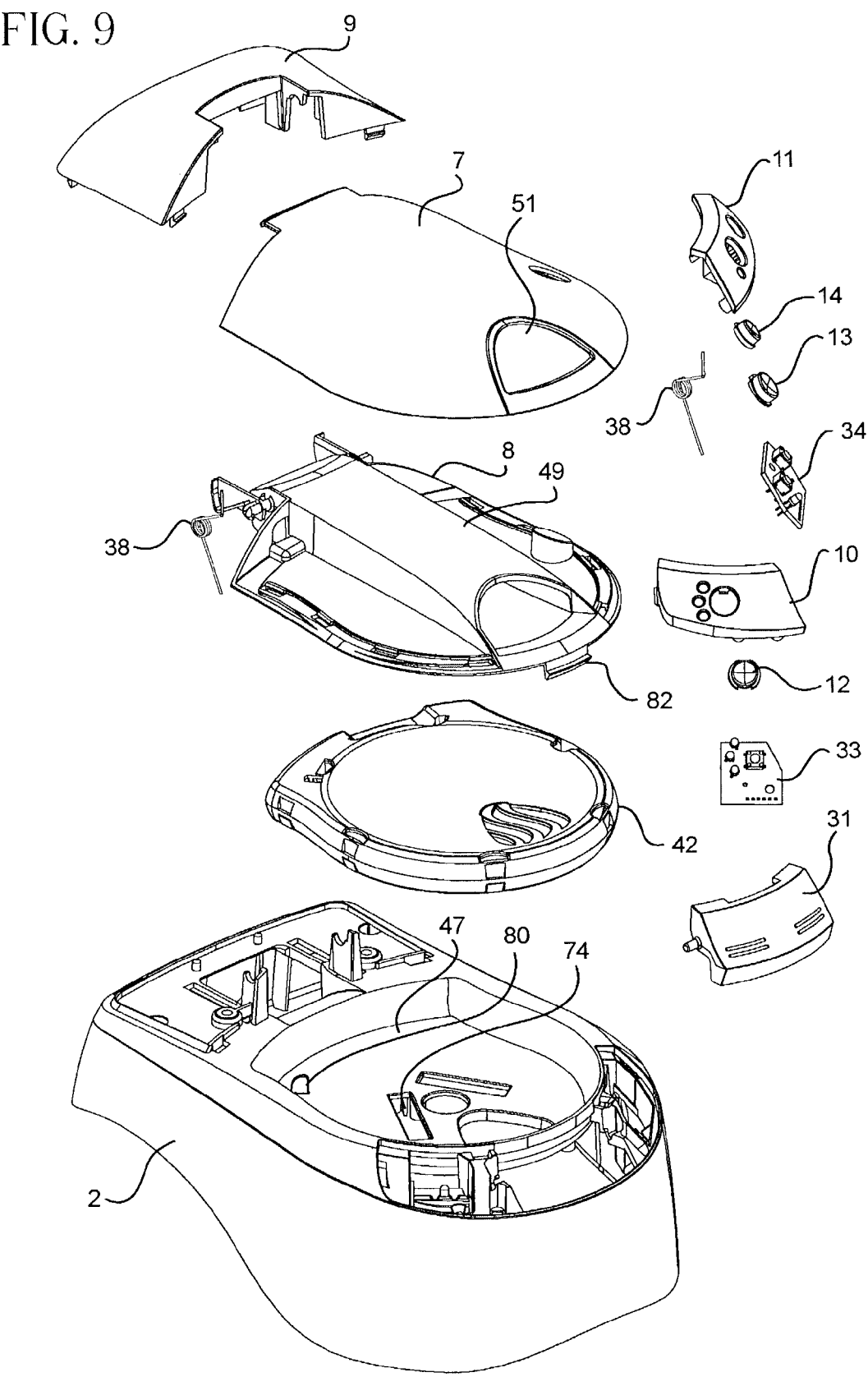
FIG. 9 is an exploded perspective view of the upper housing of the present invention.
Figure 10:
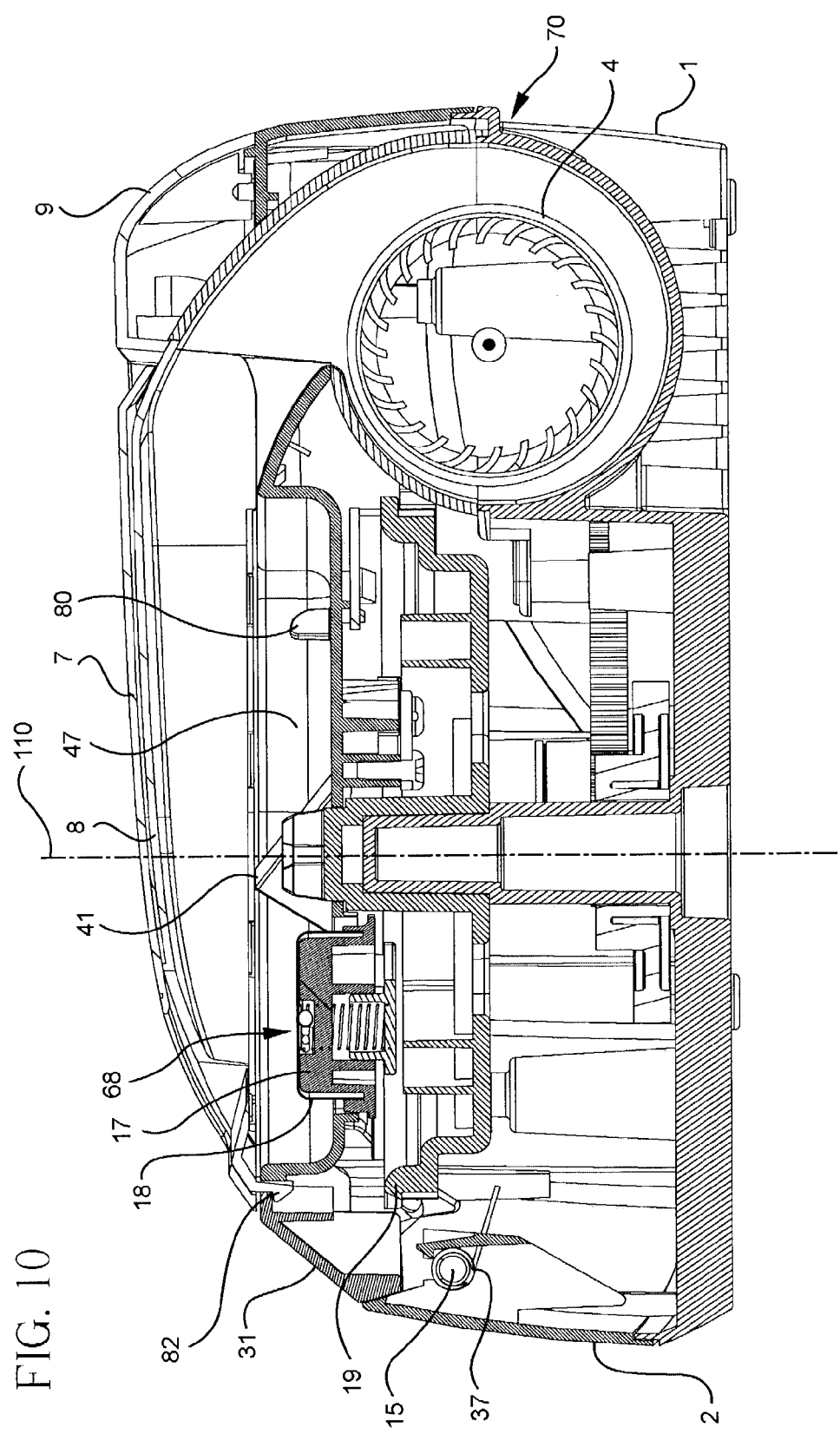
FIG. 10 is a cross-sectional view taken along line 10—10 on FIG. 2 showing the general path that the air takes through the present invention without having a cartridge installed therein.
Figure 14:
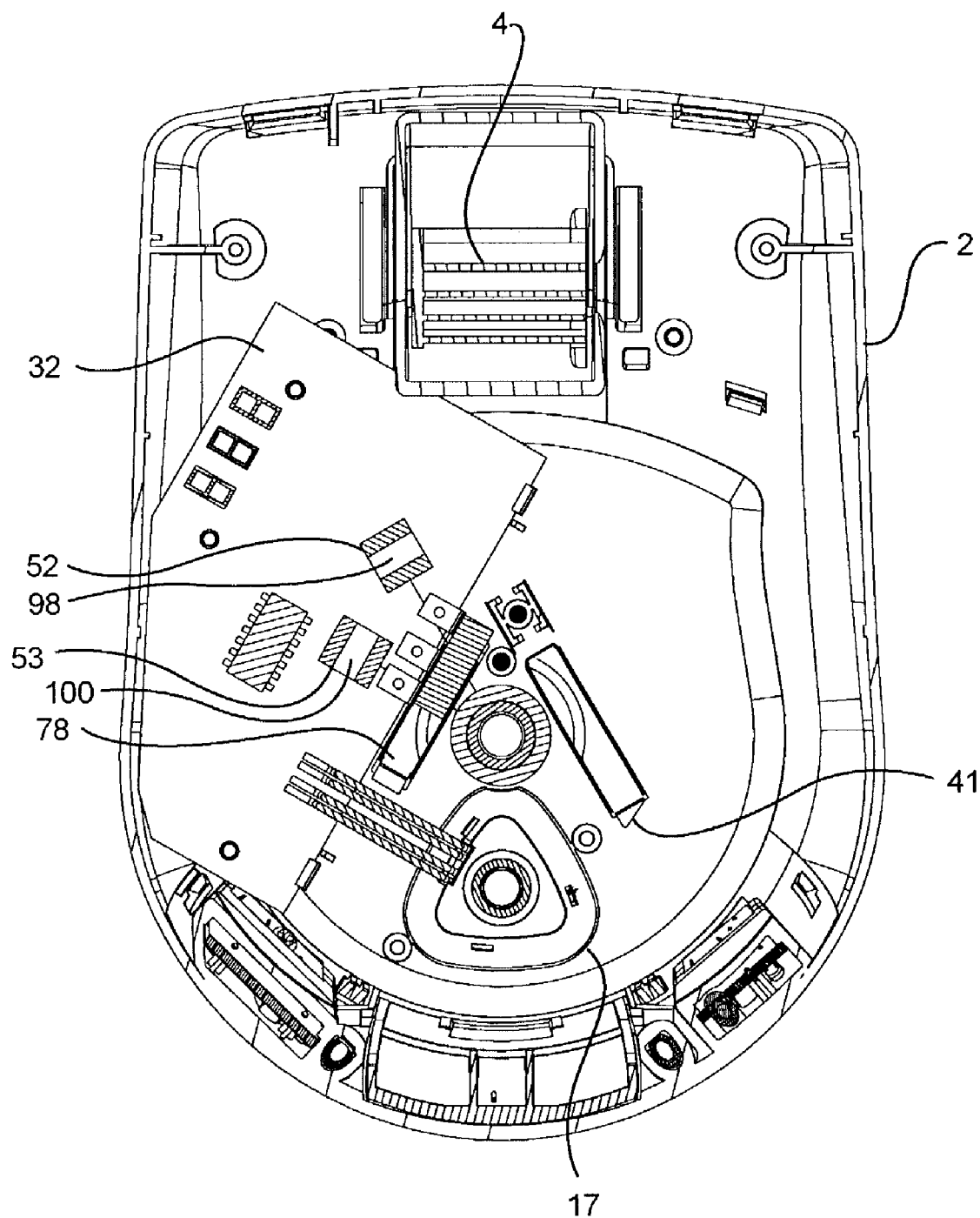
FIG. 14 is a cross-sectional view taken along line 14—14 on FIG. 3 showing the main printed circuit board and heater assembly.
Figure 15:
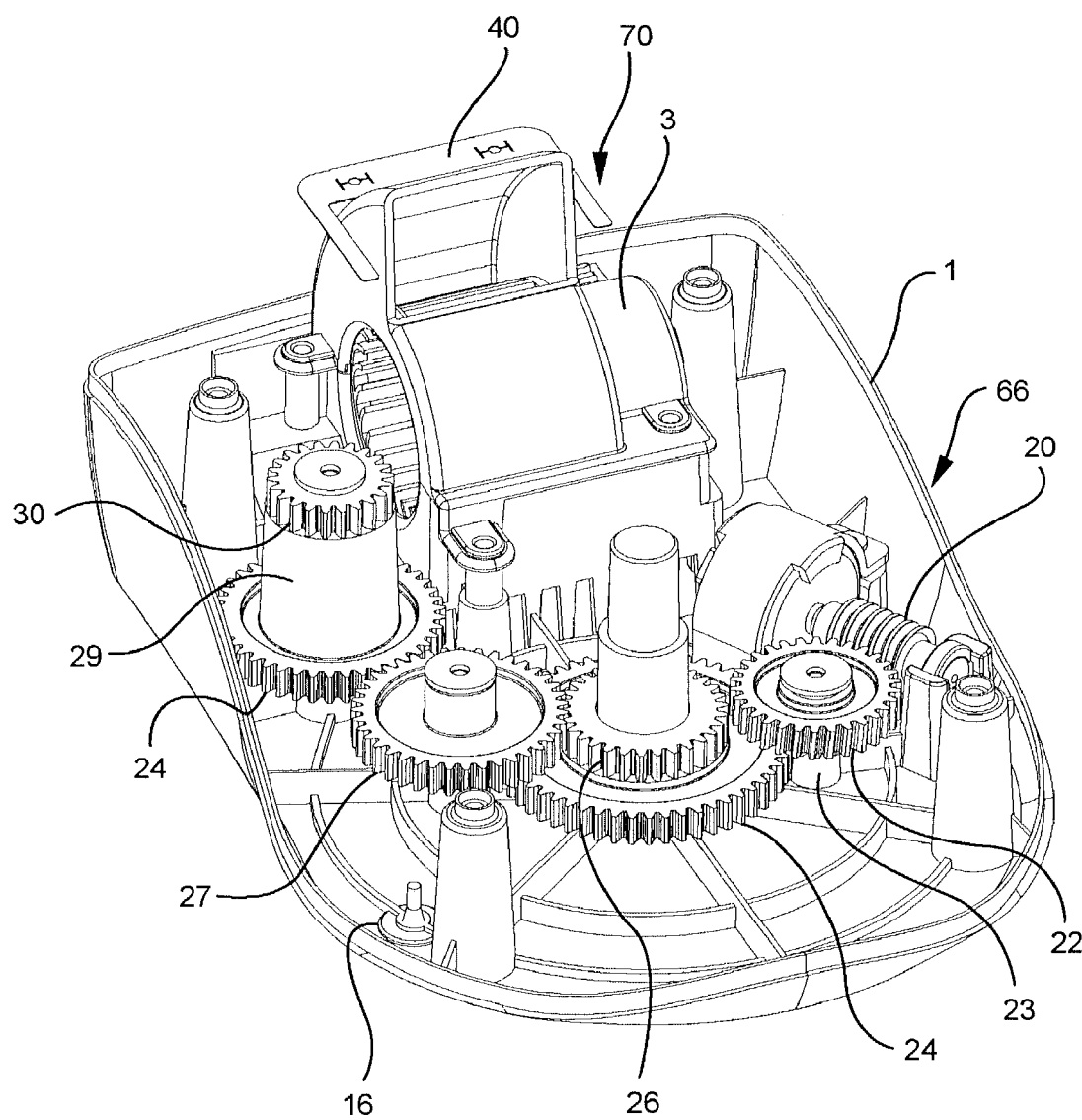
FIG. 15 is a first perspective view showing the bottom housing, drive assembly, and blower assembly of the present invention.
Figure 16:
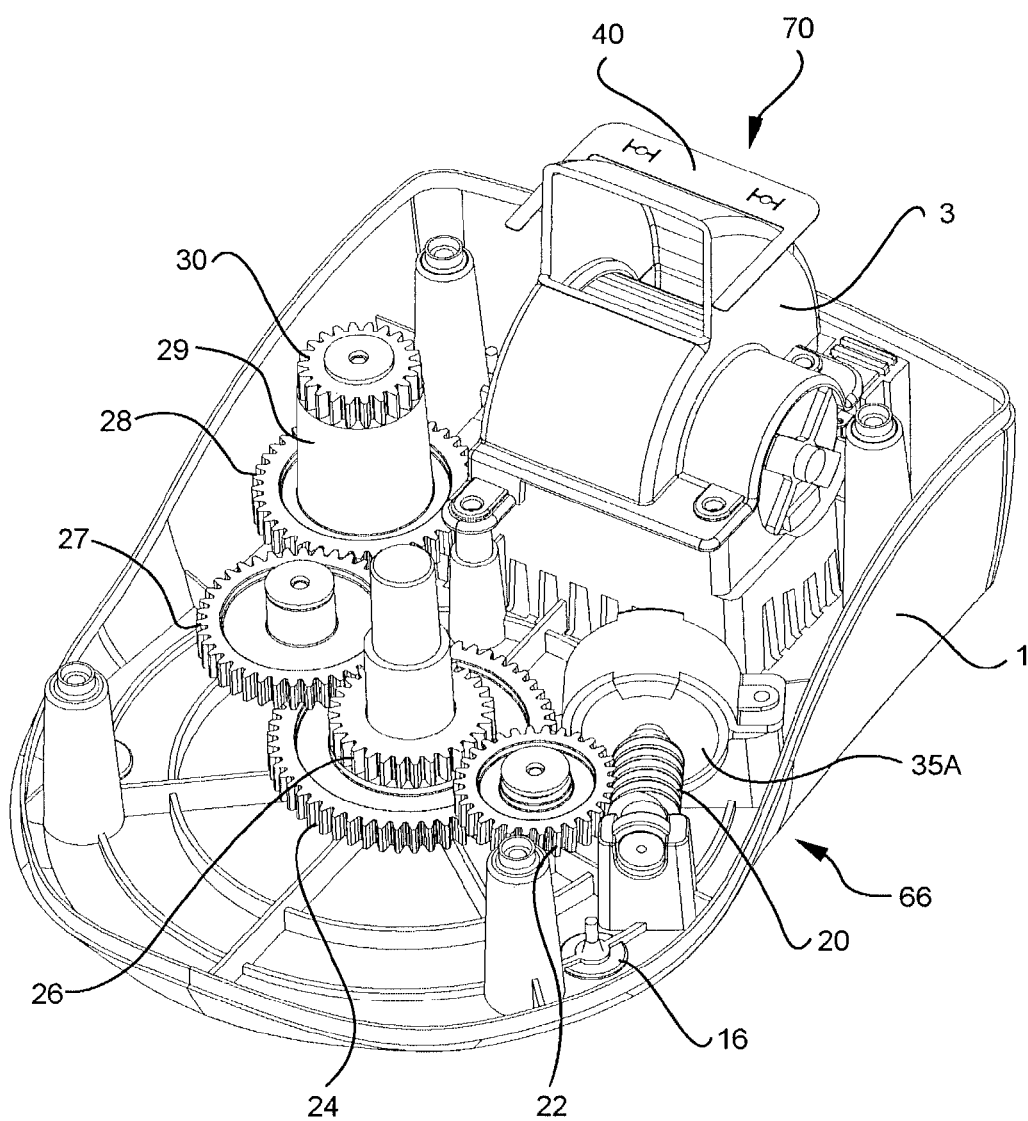
FIG. 16 is a second perspective view showing the bottom housing, drive assembly, and blower assembly of the present invention.
Figure 17:
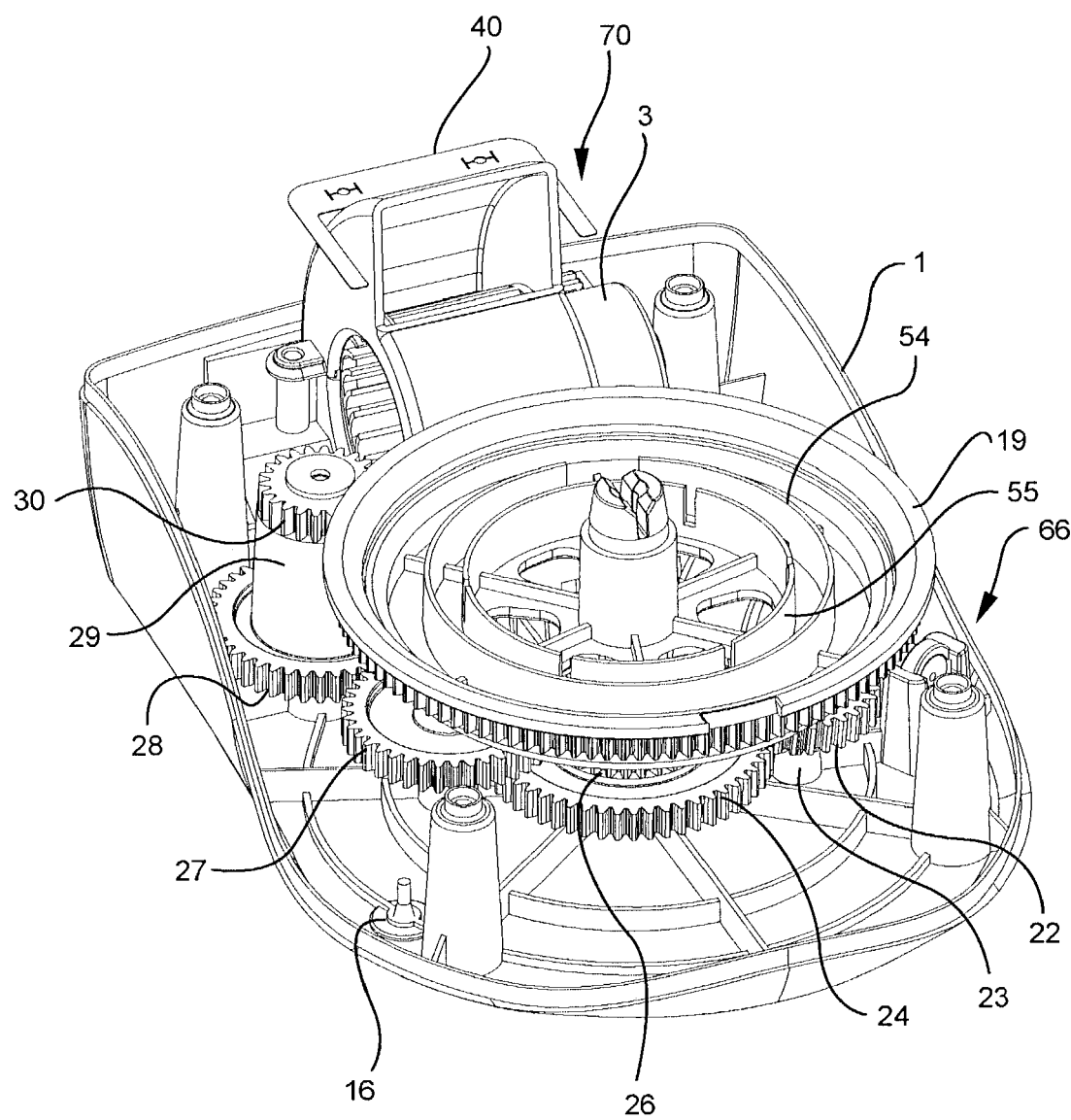
FIG. 17 is a perspective view similar to the view shown in FIG. 15 with the platter shown installed on the drive assembly.
Figure 18:
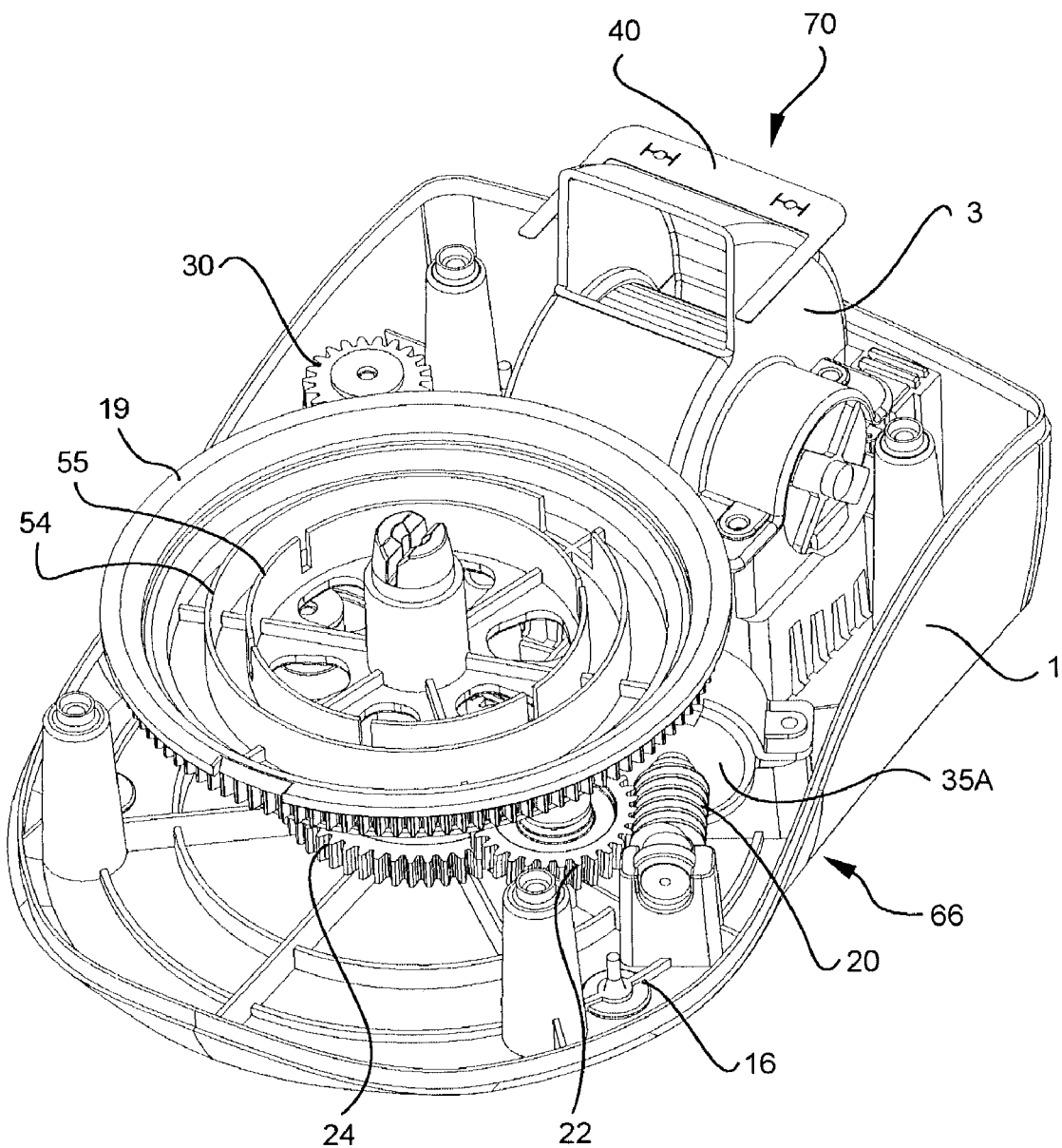
FIG. 18 is a perspective view similar to the view shown in FIG. 16 with the platter shown installed on the drive assembly.

Referring to FIGS. 15 and 16, the bottom housing 1 generally supports the drive assembly 66 and blower assembly 70 therein. The bottom housing 1 preferably includes a plurality of feet 16 made from an elastomer to provide slip resistance and to help reduce any vibrations associated the blower assembly 70 and drive assembly 66. As shown in FIGS. 9, 10, 14, the top housing 2 generally supports the heating assembly 68 and the positioning assembly 70 above the bottom housing 2. The top cap 9 is mounted to the top housing 2 and is rotatably connected to the top cover 7. The top cover 7 includes a lower portion 8 that defines a channel 49 that communicates with the blower assembly 70. The top cover 7 together with the lower portion 8 can be opened to provide access to a cartridge-receiving cavity 47 formed in the top housing 2 for installing the cartridge 42 therein. The lower portion 8 is preferably configured to cooperate with at least one torsion spring 38 and a spring damper 40 to hold the cover 7 in a substantially upright position after opening.

Figure 4:
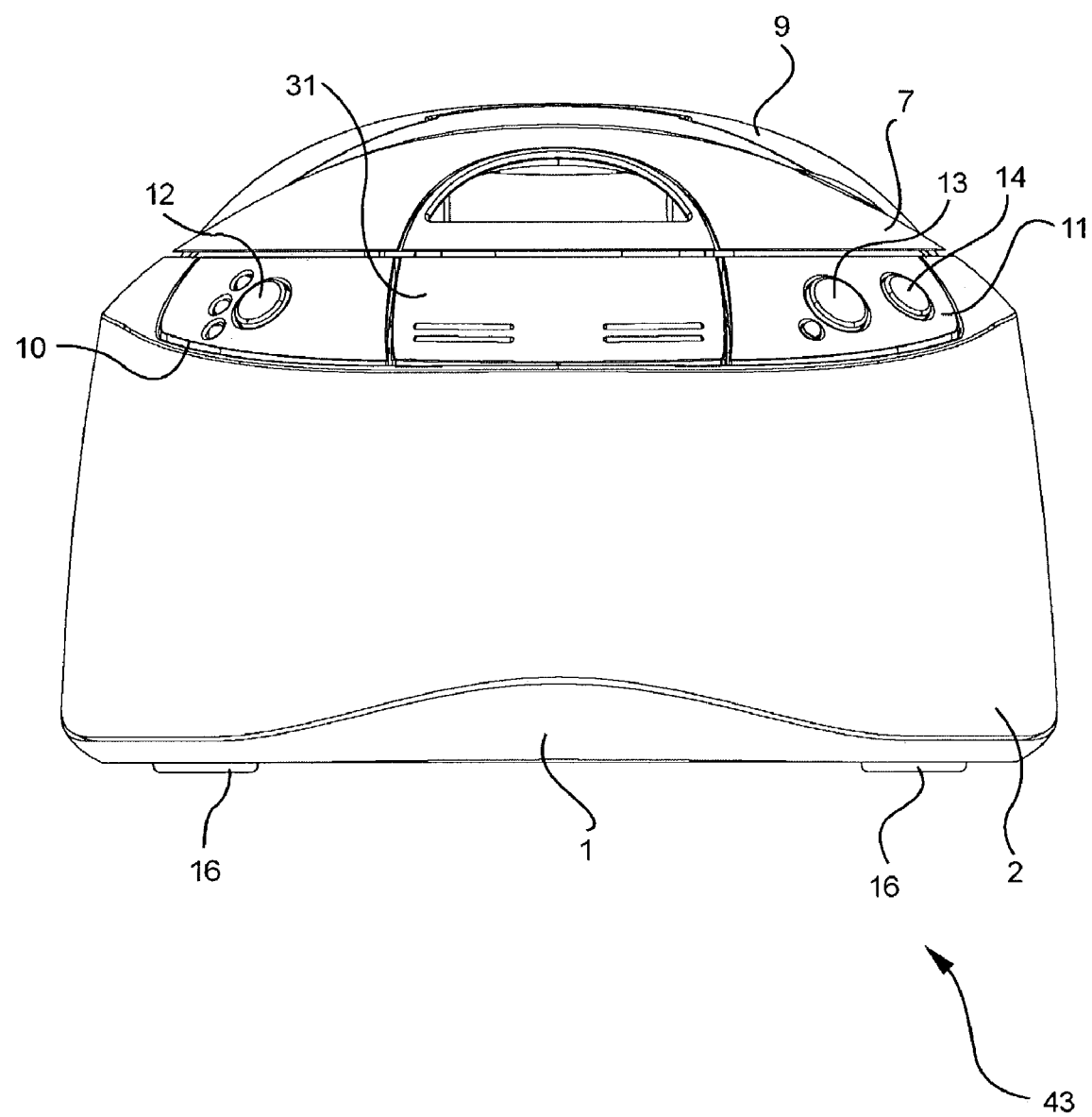
FIG. 4 is a front elevational view of the present invention.
Figure 34:
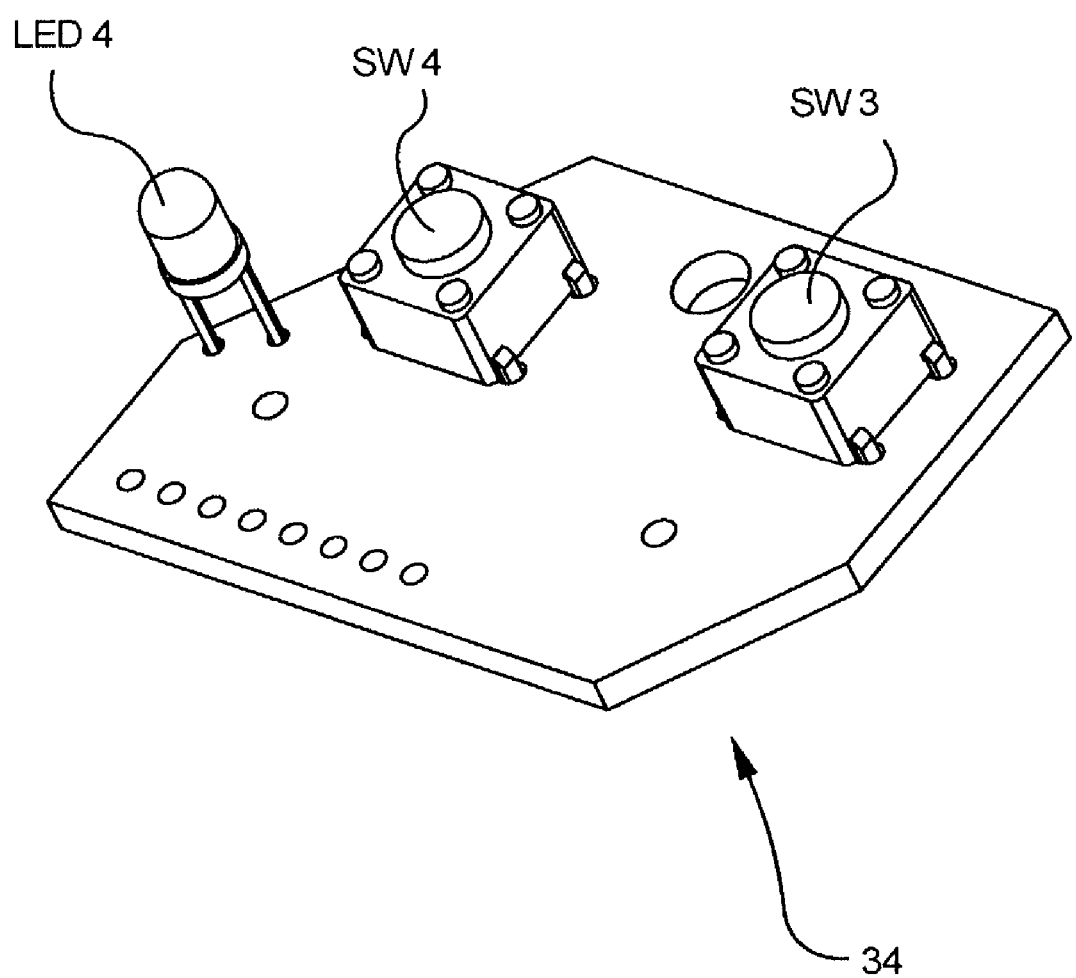
FIG. 34 is a perspective view showing the play-skip printed circuit board assembly.
Figure 35:
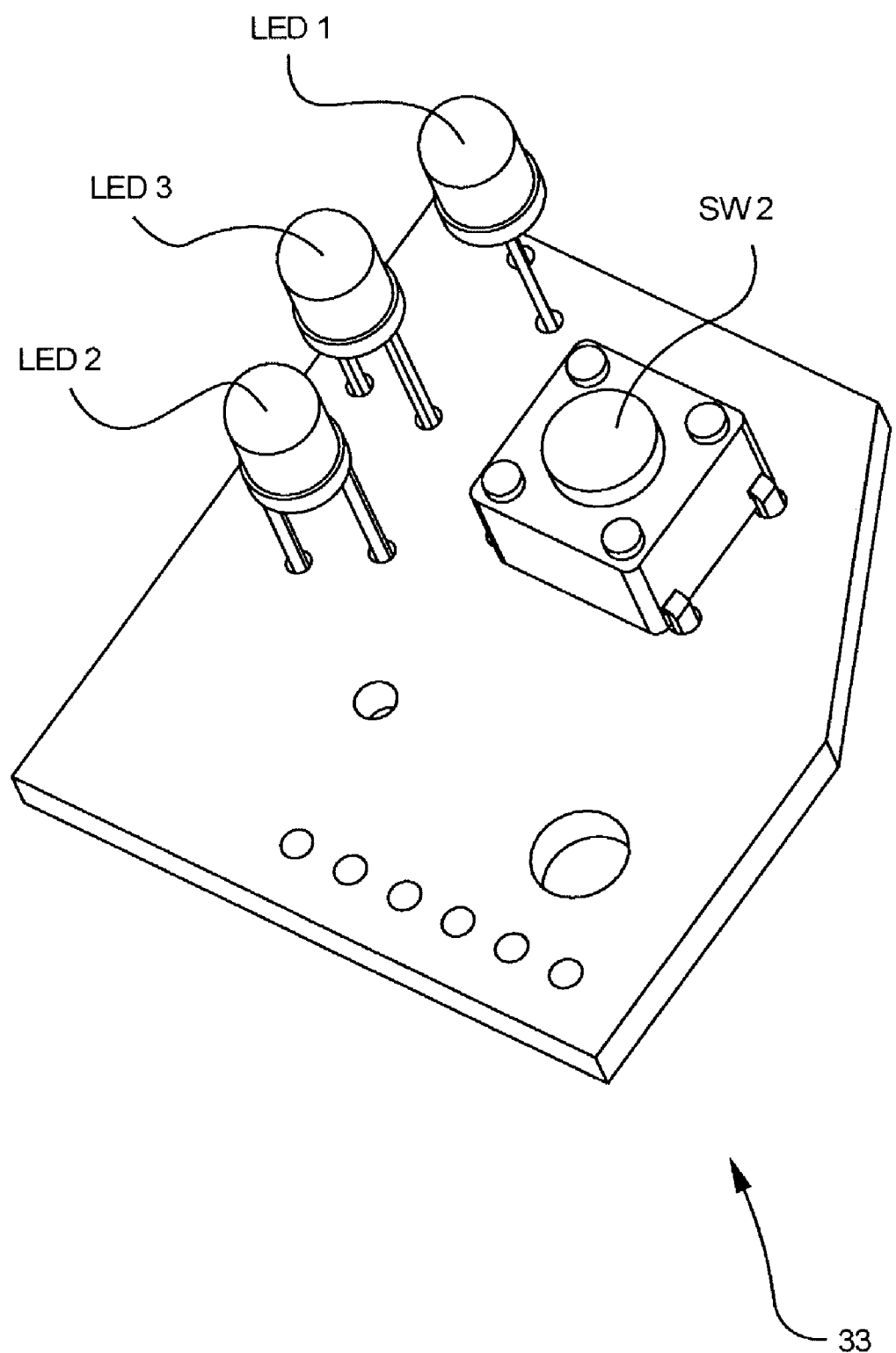
FIG. 35 is a perspective view showing the intensity printed circuit board assembly.

Referring now to FIG. 4, the housing also includes a left control panel 10, a right control panel 11, and latch 31. The left control panel 10 supports an intensity button 12 that cooperates with switch SW2 on the intensity printed circuit board 33 which is shown in FIG. 35. The right control panel 11 supports a play/stop button 13 and a skip button 14 that cooperate respectively with switches SW4 and SW3 on the play-skip printed circuit board 34 which is shown in FIG. 34.

Figure 11:
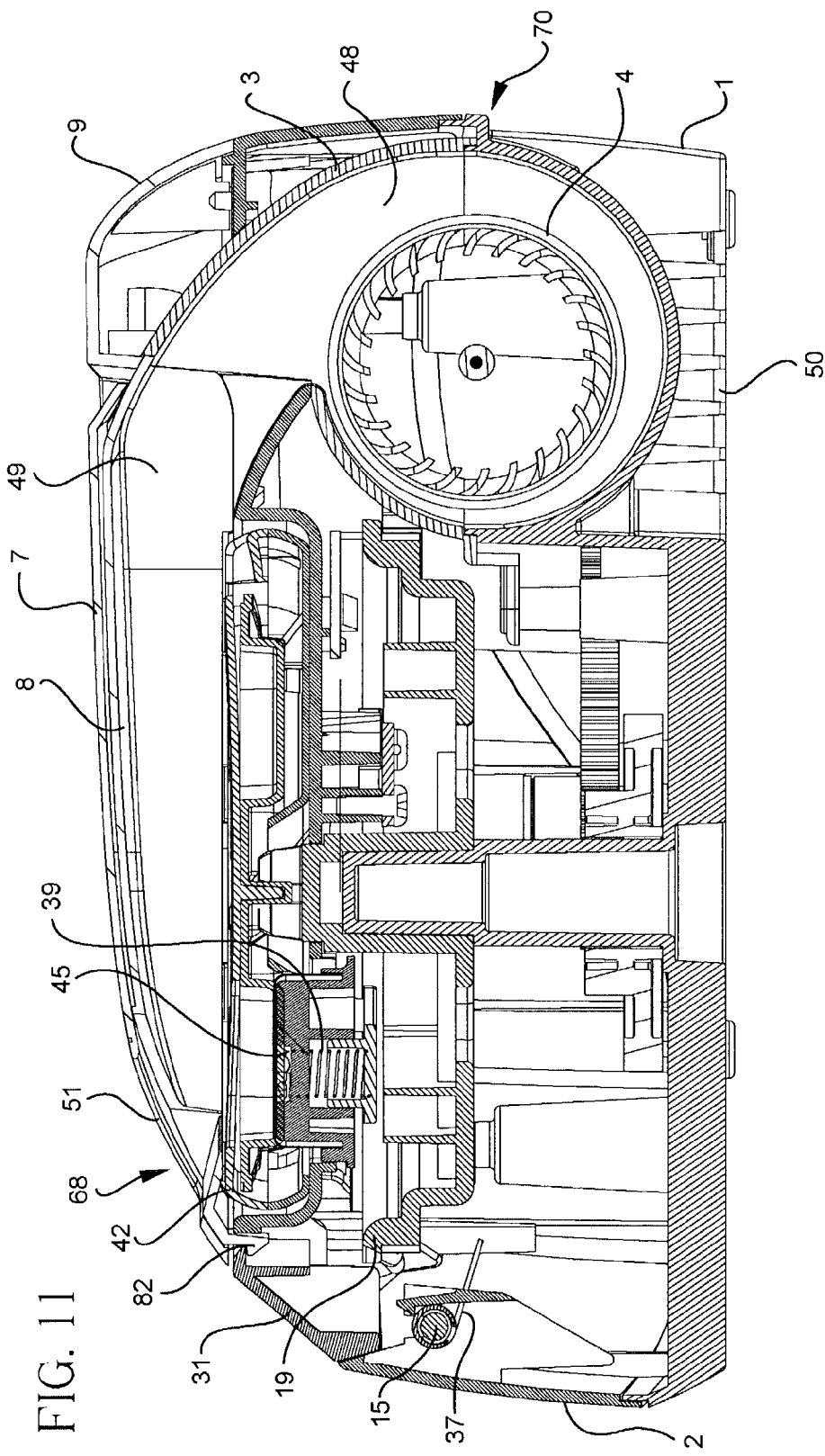
FIG. 11 is a cross-sectional view taken along line 10—10 on FIG. 2 showing the general path that the air takes through the present invention with a cartridge installed therein.
Figure 23:
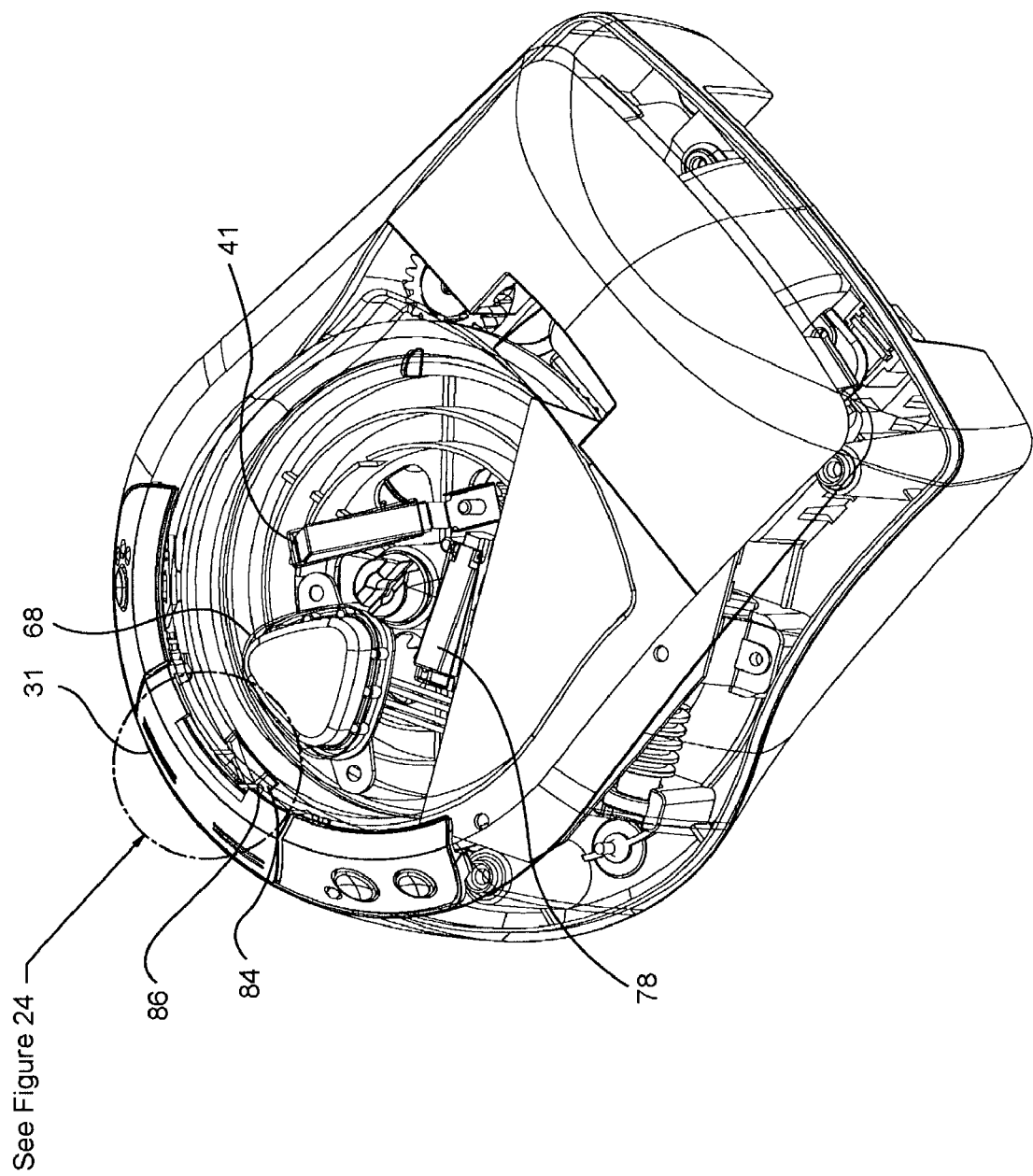
FIG. 23 is a partially cut away top perspective view similar of the present invention showing the latch engaging the platter.
Figure 24:
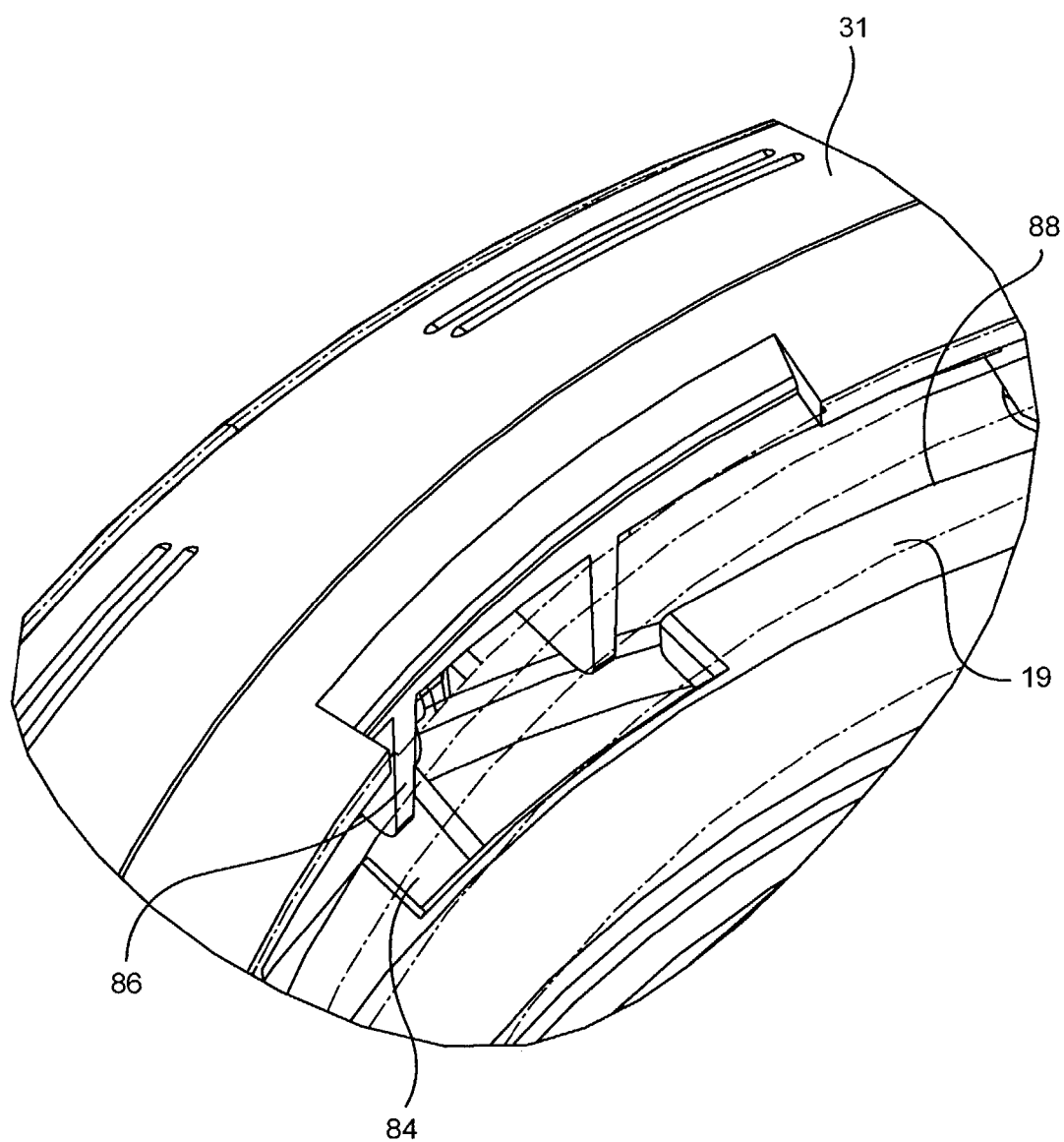
FIG. 24 is an enlarged detail of the latch engaging the platter shown in FIG. 23.

Referring initially to FIGS. 10 and 11, the latch 31 is configured to cooperate with a lip 82 formed on the lower portion 8 of the top cover 7 to maintain the top cover in a closed position as shown in FIGS. 10 and 11. The latch 31 is biased by a latch torsion spring 37 supported by a spring latch shaft 15 against the lip 82 as shown in FIG. 10 in the absence of pressure. The latch 31 preferably cooperates with the drive assembly 66 to lock the top cover 7 in a closed position after the drive assembly 66 has rotated the disk within the cartridge 42 from a home position. The drive assembly 66 and positioning assembly 72 preferably include a platter 19 that has a body 112 defined by a perimeter 88 and a center 114 with a hub 21 attached to the body 112 at the center 114, which is illustrated in FIGS. 19 through 22. The perimeter 88 is preferably formed with a latch notch 84 configured to receive a key 86 formed on the latch 31 as shown in FIGS. 23 and 24. The latch notch 84 is located on the perimeter 88 of the platter 19 corresponding to the home position of the cartridge 42. When the cartridge 42 is located in the home position, pressure applied to the latch 31 will translate the key 86 into the latch notch 84 while disengaging the latch 31 from the lip 82. However, when the cartridge 42 has been rotated out of the home position, pressure applied to the latch 31 will force the key 86 against the perimeter 88 of the platter 19 and the latch 31 will not be disengaged from the lip 82.

Figure 25:
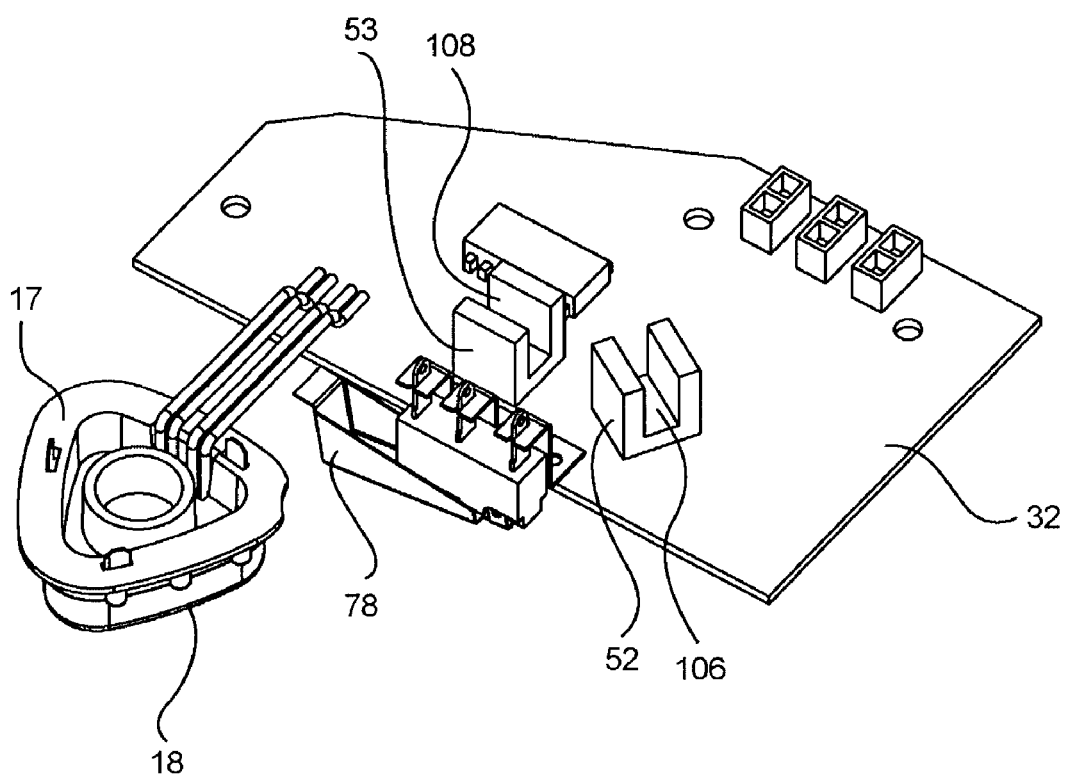
FIG. 25 is a bottom perspective view showing the main printed circuit board and a portion of the heater assembly.
Figure 32:
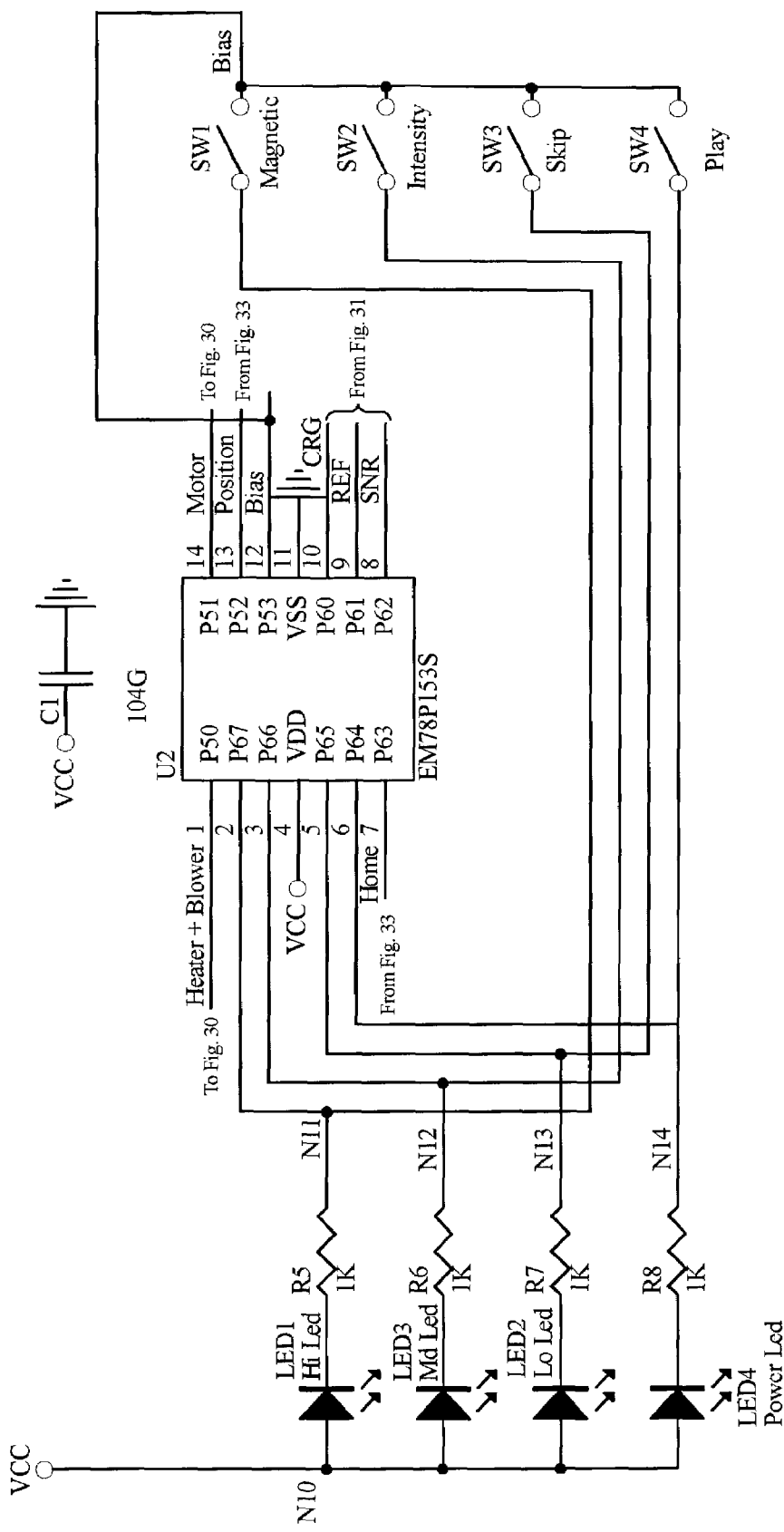
FIG. 32 is a schematic diagram of a circuit.

Referring now to FIGS. 8, 9, 10, 14, 23, and 25, the cartridge-receiving cavity 47 formed in the top housing 2 includes first and second rectangular shaped openings 74, 76 configured to cooperate respectively with an ejection member 41 and an electrical switch 78 (corresponding to switch SW1 shown on FIG. 32). Referring now to FIG. 10, the ejection member 41 is spring loaded to assist in removing a cartridge 42 that is installed in the cartridge-receiving cavity 47. The electrical switch 78 is supported by the main printed circuit board 32 as shown in FIG. 25 and cuts off current to the main printed circuit board 32 unless a cartridge 42 is installed in the cartridge-receiving cavity 47. The cartridge-receiving cavity 47 is also preferably formed with a tab 80 for engaging the cartridge 42. The cartridge 42 can be configured to cooperate with the tab 80 to not allow the disk within the cartridge 42 to rotate unless the cartridge 42 engages the tab 80.

Figure 7:
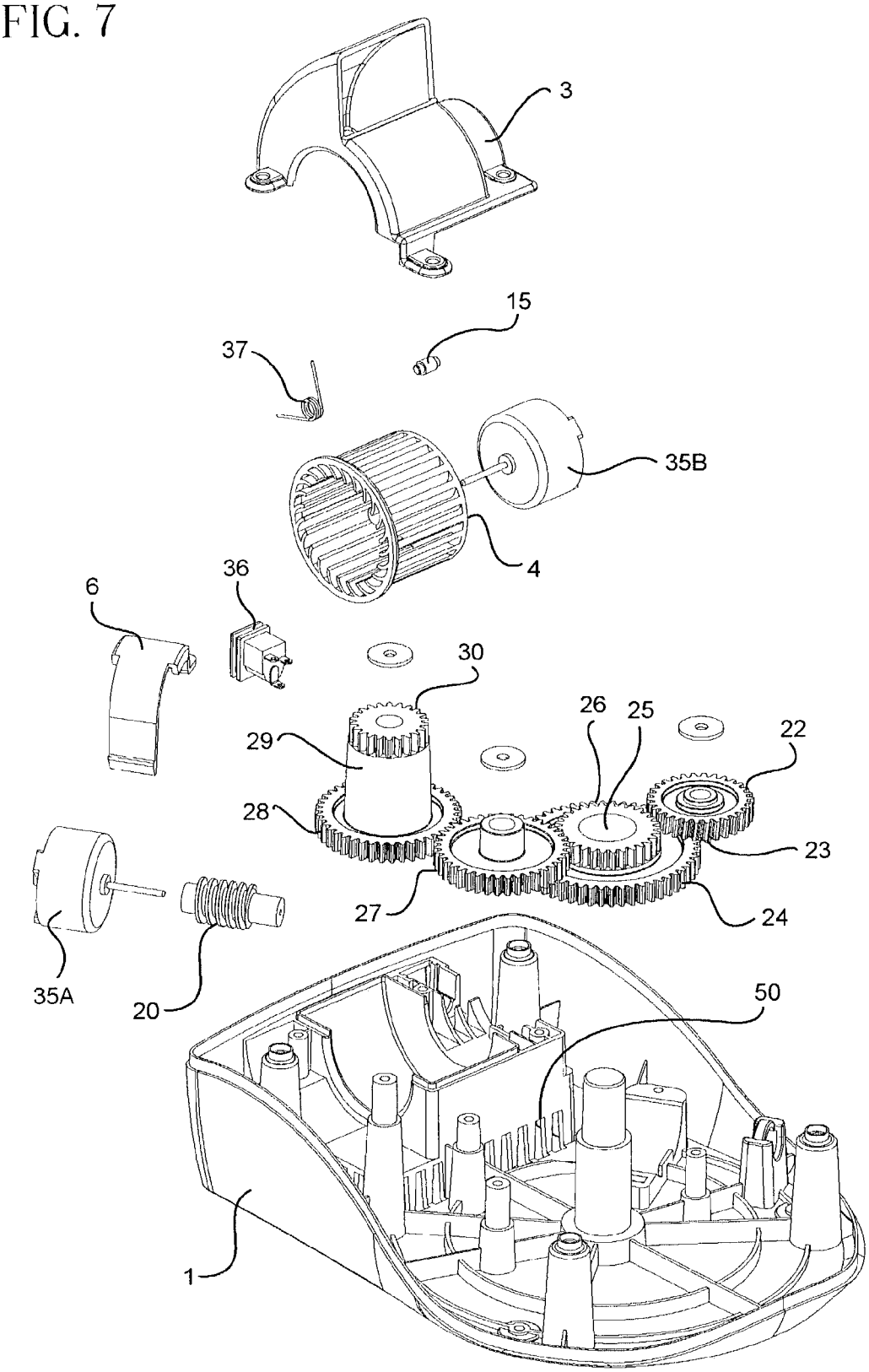
FIG. 7 is an exploded perspective view of the bottom housing, blower assembly, and portion of the platter drive assembly of the present invention.
Figure 13:
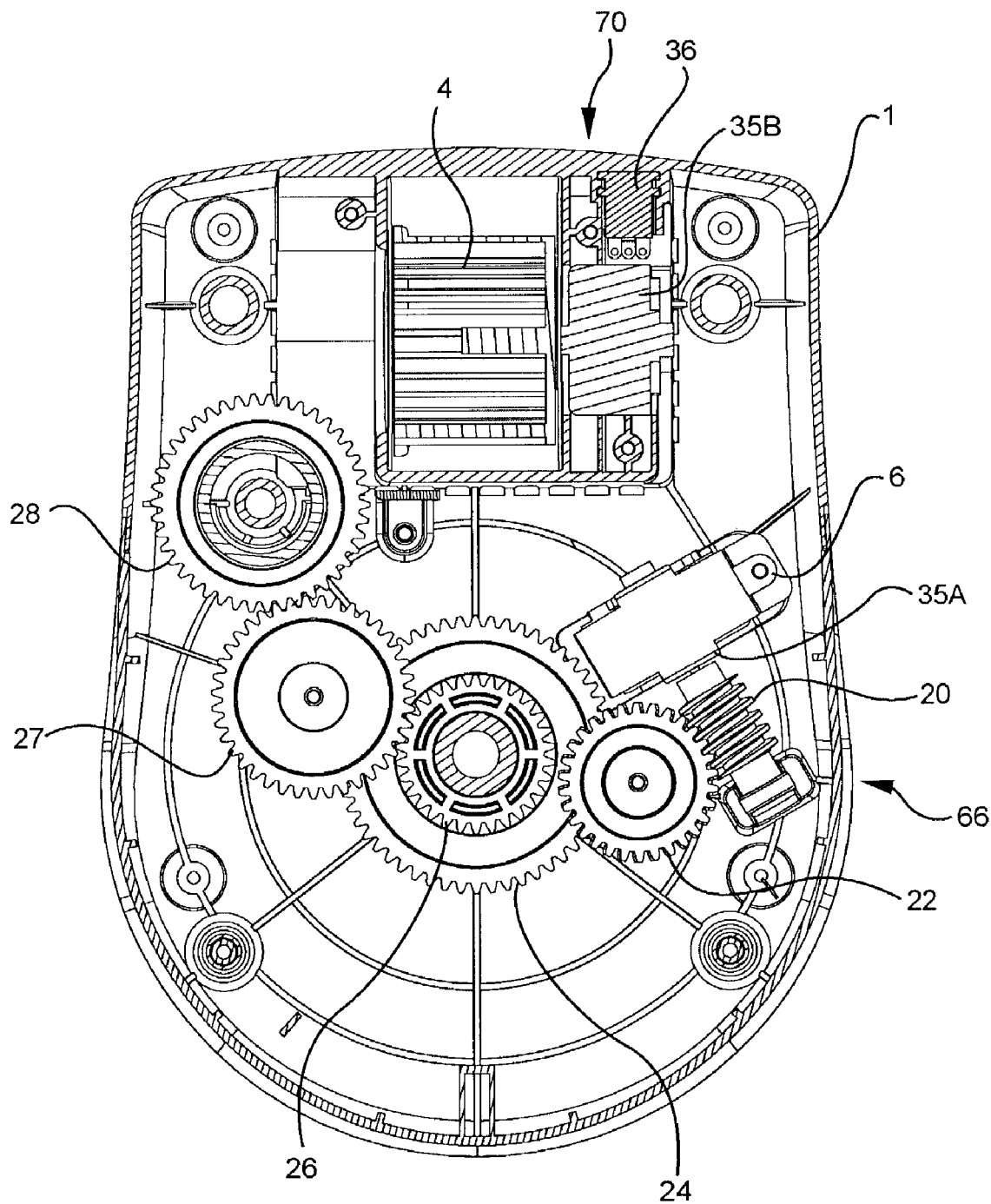
FIG. 13 is a cross-sectional view taken along line 13—13 on FIG. 3 showing a portion of the drive assembly and blower asssembly.

Referring now to FIGS. 7, 13, and 15 through 18, the drive assembly 66 is mounted within the bottom housing 1 and includes a motor 35A and a plurality of gears 19, 20, 22, 23, 24, 26, 27, 28, 30 arranged to rotate a hub 21 about an axis of rotation 110. The hub 21 is configured to engage the rotatable disk within the cartridge 42. The motor 35A is preferably a DC powered motor that operates at about 12 volts to produce a torque of about 0.4 in-lbs with a motor speed about 250 r.p.m. A suitable motor is model WRF-500TB-12560 No. WCG-004Y-017 manufactured by Shenzhen Weizhen Motor Co., LTD. The motor 35A is preferably mounted to the bottom housing 1 by a motor retainer 6 as shown in FIGS. 7 and 13. The 12 volts of DC current is preferably provided through an external power pack that is configured to cooperate with jack 36 shown in FIGS. 5 and 7. The plurality of gears combine generally for about an overall 953:1 gear reduction to deliver at least 5 in-lbs torque at about a 3 second per revolution speed to the hub 21.

The overall 953:1 gear reduction is accomplished through the reduction by the separate combinations of the individual gears. The individual gears are generally defined by parameters including: outside diameter, pitch diameter, teeth number, pitch, and pressure angle. In a preferred embodiment of the invention, these parameters are about as follows:

| Gear | Outside Diameter (millimeters) | Pitch Diameter (millimeters) | Number of gear teeth | Pitch (English) | Pressure Angle |
|---|---|---|---|---|---|
| platter 19 | 119.56 | 117.45 | 111 | 24 | 20 degree |
| worm 20 | 14.81 | 12.7 (.500 inch) | helical single thread to match worm gear 22 | 24 | 14.5 |
| worm gear 22 | 33.86 | 31.75 (1.250 inch) | 30 | 24 | 14.5 |
| first small gear 23 | 14.81 | 12.7 (.500 inch) | 12 | 24 | 20 degree |
| second large gear 24 | 59.26 | 57.15 (2.250 inch) | 54 | 24 | 20 degree |
| second small gear 26 | 33.86 | 31.75 (1.250 inch) | 30 | 24 | 20 degree |
| third gear 27 | 43.38 | 41.28 (1.625 inch) | 39 | 24 | 20 degree |
| fourth | 46.56 | 44.45 | 42 | 24 | 20 degree |

-continued

| Gear | Outside Diameter (millimeters) | Pitch Diameter (millimeters) | Number of gear teeth | Pitch (English) | Pressure Angle |
|---|---|---|---|---|---|
| large gear 28 | | (1.750 inch) | | | |
| fourth small gear 30 | 25.4 | 23.19 (.917 inch) | 22 | 24 | 20 degree |

The motor 35A is coupled to the worm 20 which engages worm gear 22. The worm gear 22 is coupled to first small gear 23 which engages second large gear 24. The second large gear 24 is preferably coupled to second small gear 26 by a second gear sleeve 25. The second small gear 26 engages third gear 27 which in turn engages fourth large gear 28. The fourth large gear 28 is coupled to fourth small gear 30 by a fourth gear sleeve 29. The fourth small gear 30 engages the platter 19 which has the hub 21 mounted thereon.

Figure 8:
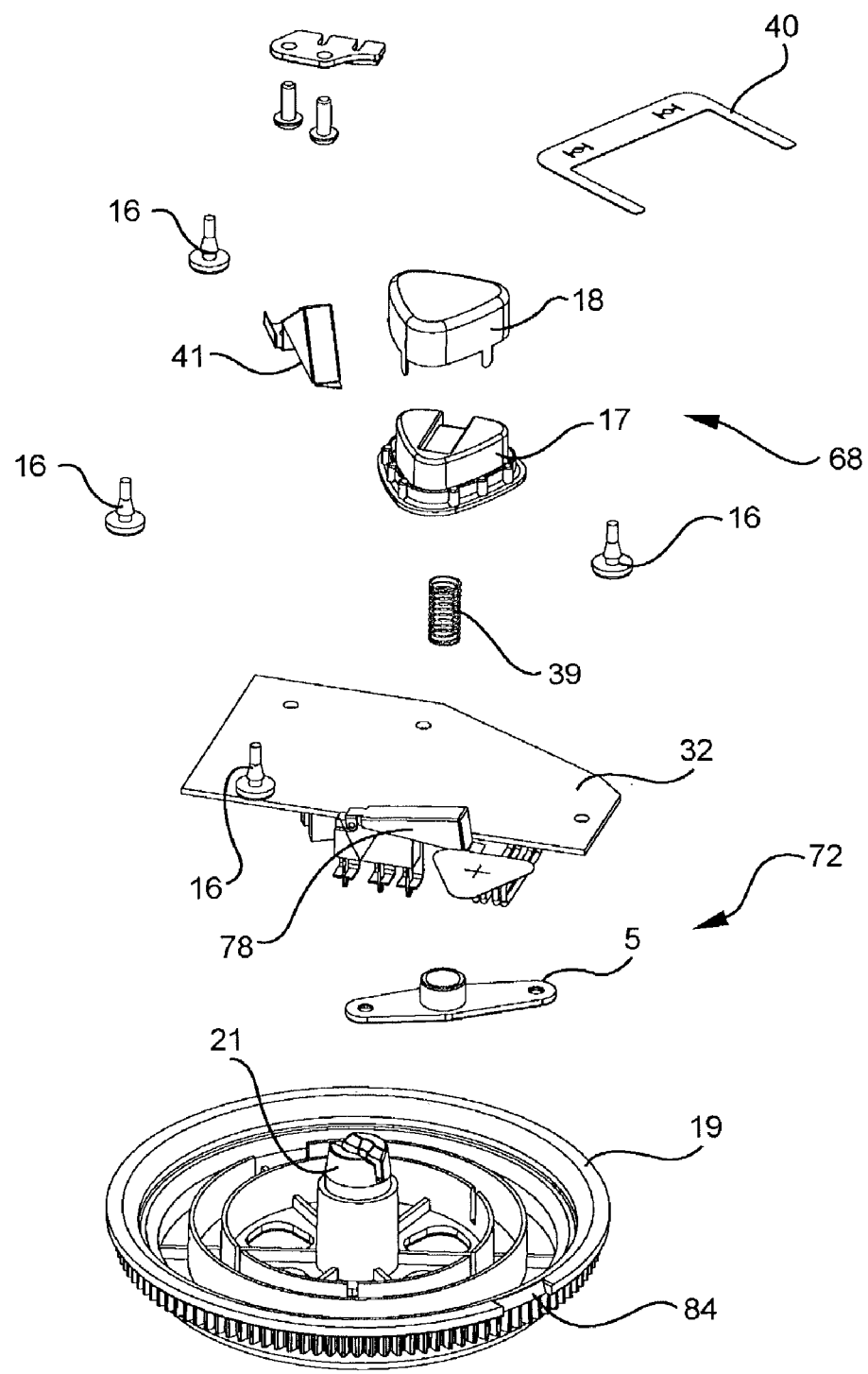
FIG. 8 is an exploded perspective view of the platter, heater assembly, and the main printed circuit board of the present invention.

Referring to FIGS. 8, 11, 25, the heating assembly 68 generally includes a heating element 45 mounted to the top housing 2 within the device 43 and is configured to reach a temperature in a range from about 60 to about 120 degrees Celsius. The heating element 45 can be a resistive type heating element, and is preferably enclosed between a heater cover 18 and a heater plunger 17. Referring to FIG. 10, the heating assembly 68 is configured to have a portion of the heater cover 18 protrude through a heater opening 46 in the cartridge-receiving cavity 47 formed in the top housing 2 before the cartridge 42 is installed. The heater cover 18 is preferably made from a metal such as stainless steel. The heater plunger 17 is preferably formed from a heat resistant plastic such as PBT (Polybutylene Terephthalate). The heating assembly 68 preferably includes a spring 39 to bias the heating element 45 against the cartridge 42 to ensure that the scent element within the cartridge 42 is heated efficiently as shown in FIG. 11. The spring 39 is supported by a retainer 5 which is connected to the top housing 2. The heating element 45 is preferably selected so that it can be operated at various temperatures for adjusting the amount of scent element that is activated. The temperature of the heating element 45 can generally be adjusted by controlling the amount of current that passes through the heating element 45 over a given period of time. This can generally be accomplished by either regulating a constant value of current that is delivered to the heating element 45 in a substantially continuous manner, or by controlling the timing of sequentially pulsing the current that is delivered to the heating element 45.

Figure 12:
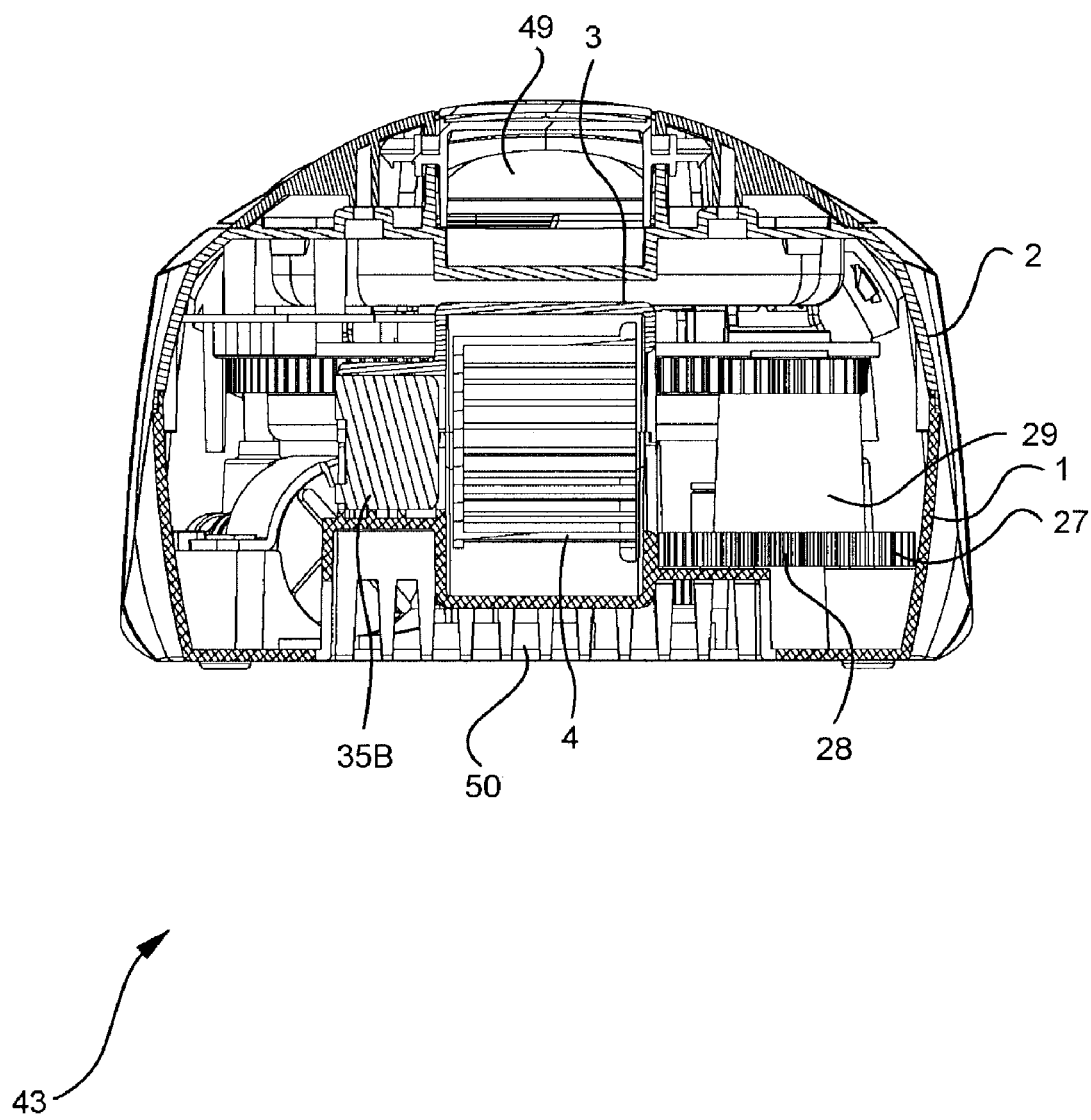
FIG. 12 is a cross-sectional view taken along line 12—12 on FIG. 3 showing a portion of the drive assembly and blower asssembly.

Referring initially to FIGS. 7, 11 and 15, the blower assembly 70 is mounted within the bottom housing 1 and generally includes a blower wheel 4 and a motor 35B. The motor 35B is preferably a DC powered motor that operates at about 12 volts. A suitable motor is model WRF-500TB-12560 No. WCG-004Y-017 manufactured by Shenzhen Weizhen Motor Co., LTD. The motor 35B is preferably mounted to the bottom housing 1 and is retained therein by a portion of a blower housing 3 as shown in FIG. 12. The blower wheel 4 is preferably a forward curved centrifugal blower which draws air in axially to the center and then expels the air out radially into a scroll 48 formed by the bottom housing 2 and the blower housing 3. The air is drawn into the blower wheel 4 from an air intake defined by openings 50 formed in the bottom housing 2 at the bottom and rear of the device 43. The scroll 48 is arranged to direct the resulting airflow through a channel 49 formed in the lower portion of the top cover 8. The channel 49 directs the airflow over the cartridge-receiving cavity 47 to diffuse a scent element corresponding to the location of the heater element 45. As the airflow passes over an activated scent element, the airflow captures the resulting volatized materials and carries them out through an exhaust port 51 formed in the top cover 7.

Figure 26:
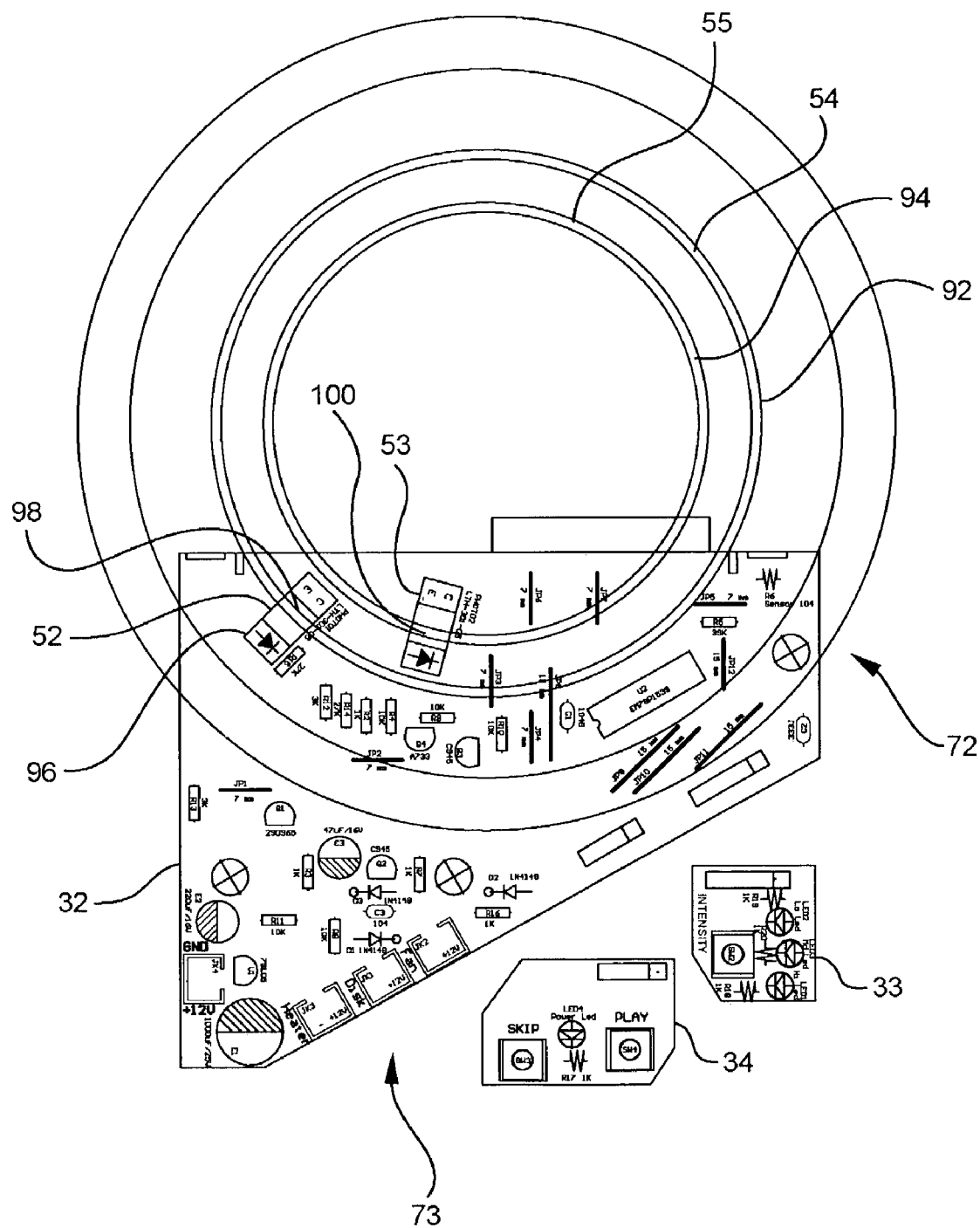
FIG. 26 is a first schematic view of the control unit shown in relationship to the platter.
Figure 27:
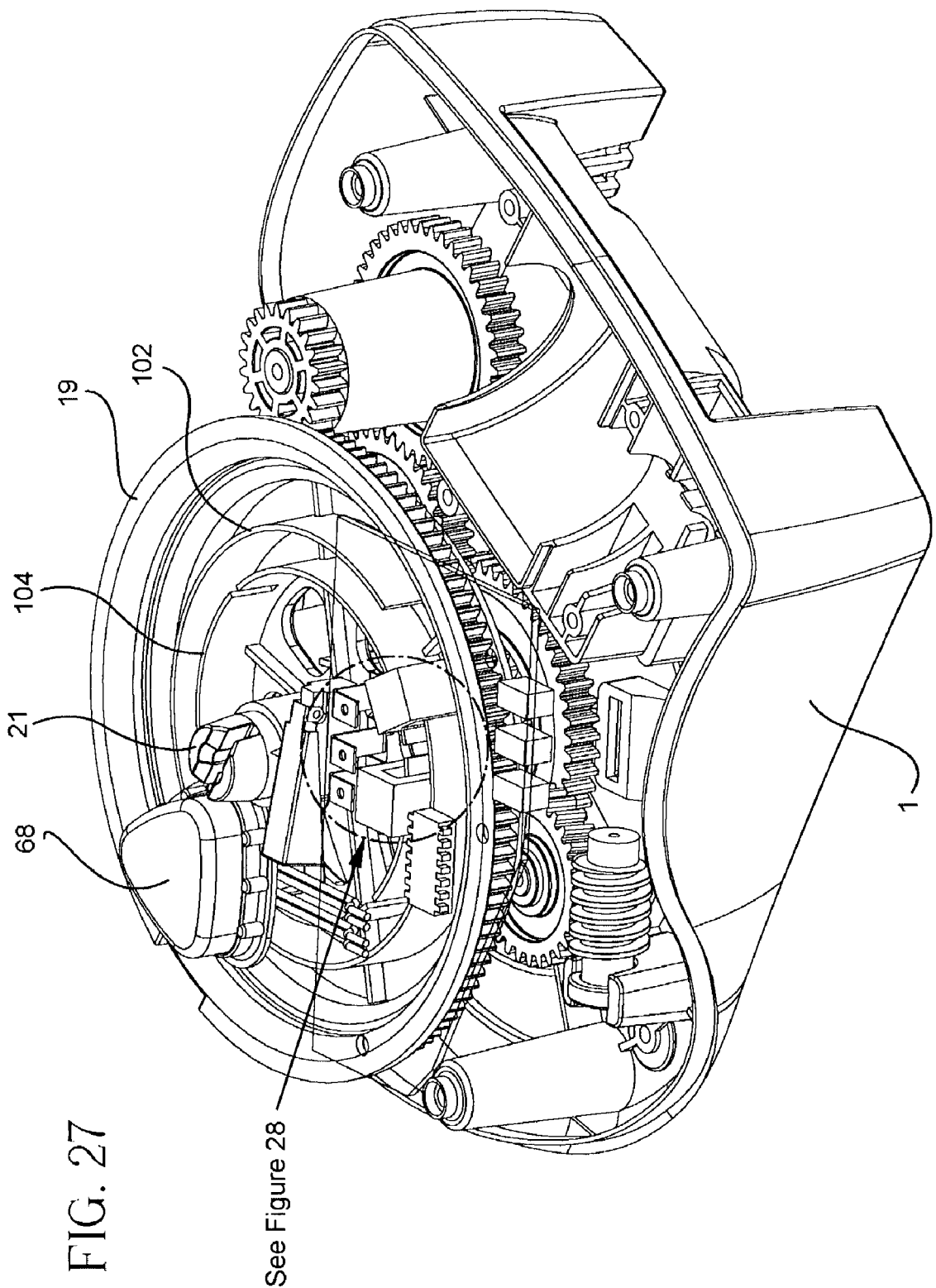
FIG. 27 is a perspective view showing the bottom housing, platter drive assembly, main printed circuit board and a portion of the heater assembly.

Referring initially to FIGS. 26 and 27, the positioning assembly 72 monitors the rotation of the hub 21 of the drive assembly 66 which in turn controls the positioning of the scent elements located within the cartridge 42. The positioning assembly 72 generally includes at least one position indicator 90 attached to the platter 19 to rotate through a circular path 92 and at least one sensor 96 arranged adjacent to a point 98 on the circular path 92 for generating a signal when the position indicator 90 is rotated to the point 98. In a first preferred embodiment of the positioning 72 assembly, the at least one position indicator 90 is a first ring 54 formed with at least one notch 56 attached to the platter 19 and the sensor 96 is an optical sensor 52 which is preferably mounted to the main printed circuit board assembly 32 as shown in FIGS. 14 and 25.

Figure 2:
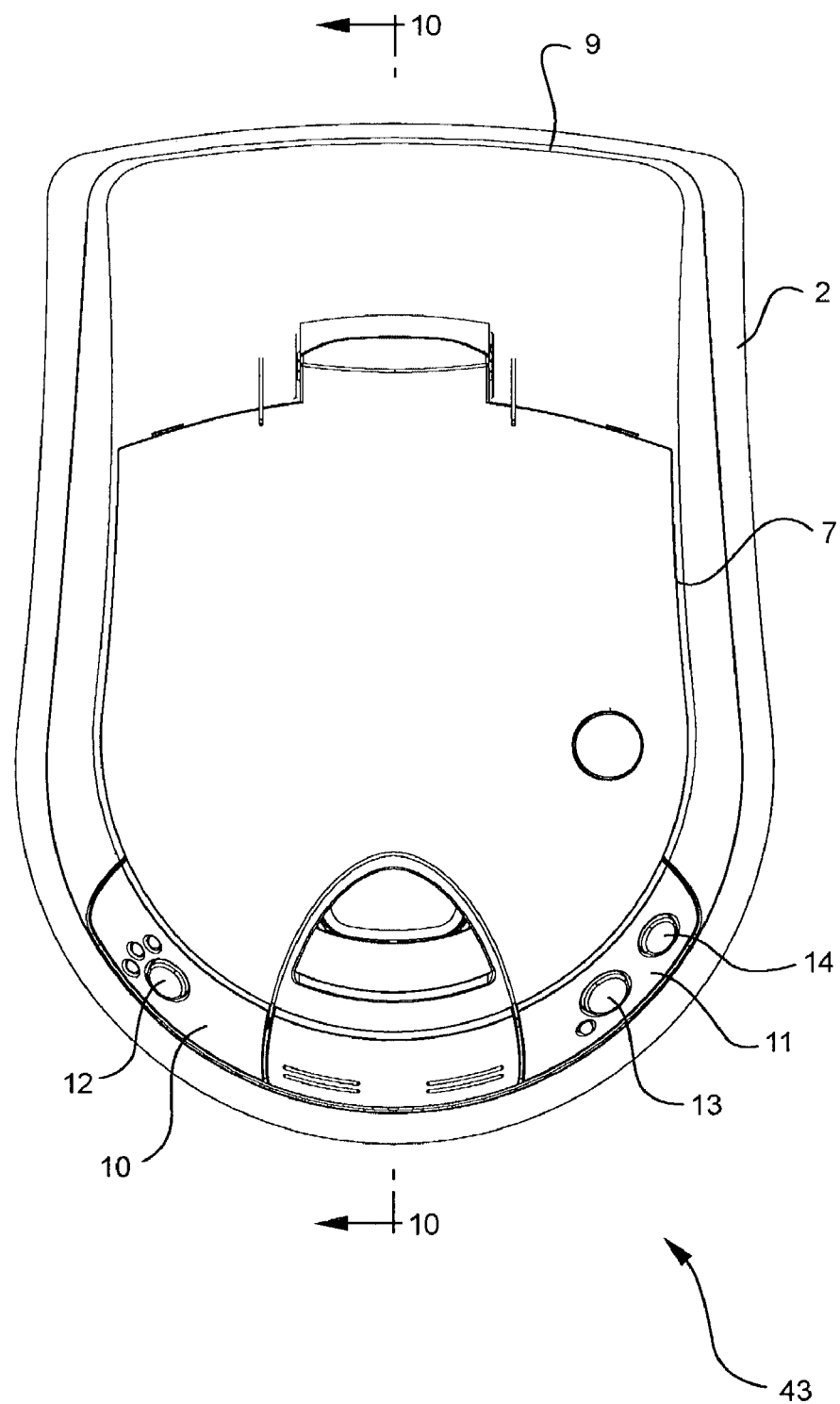
FIG. 2 is a top plan view of the present invention.
Figure 3:
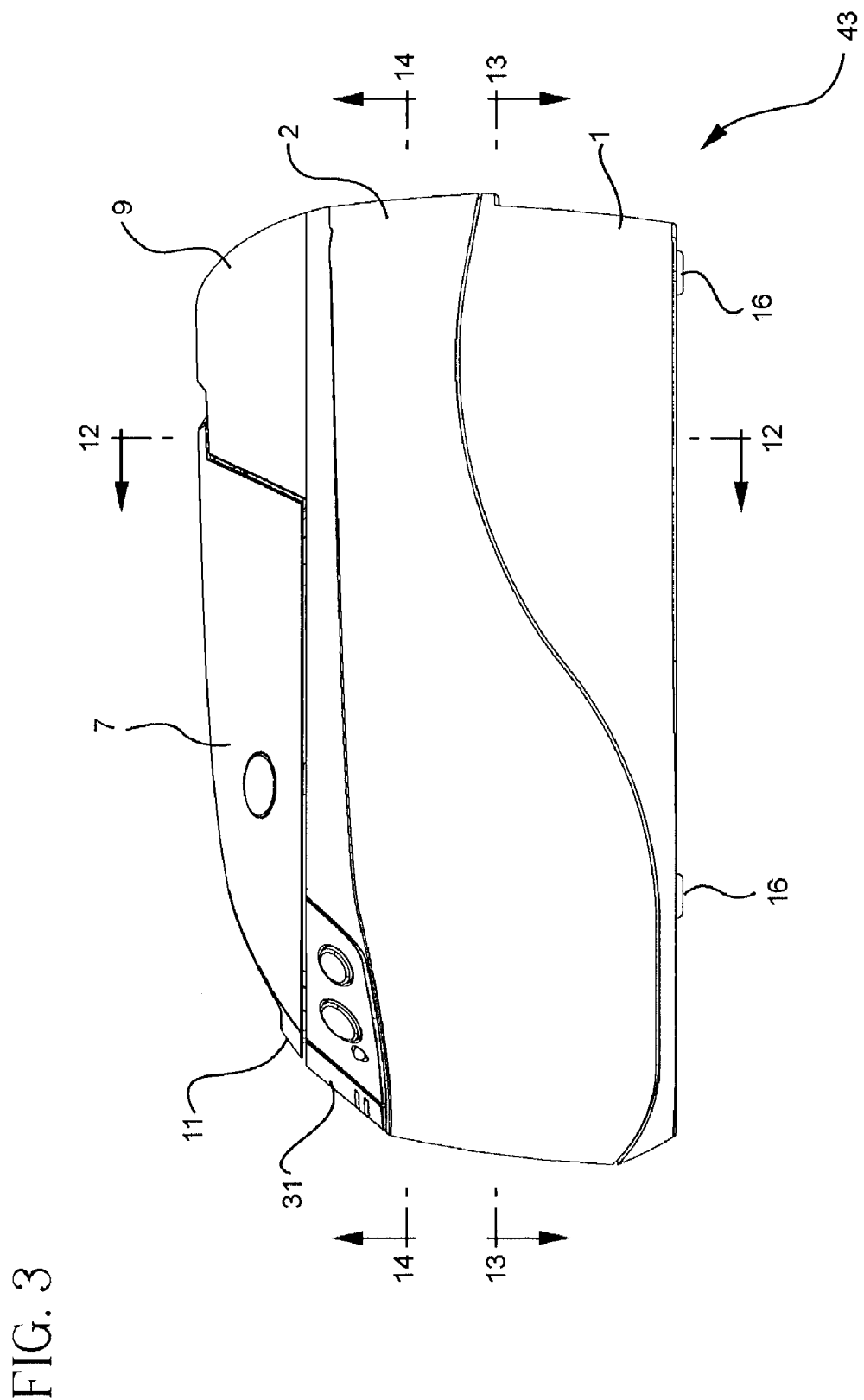
FIG. 3 is a side elevational view of the present invention.
Figure 33:
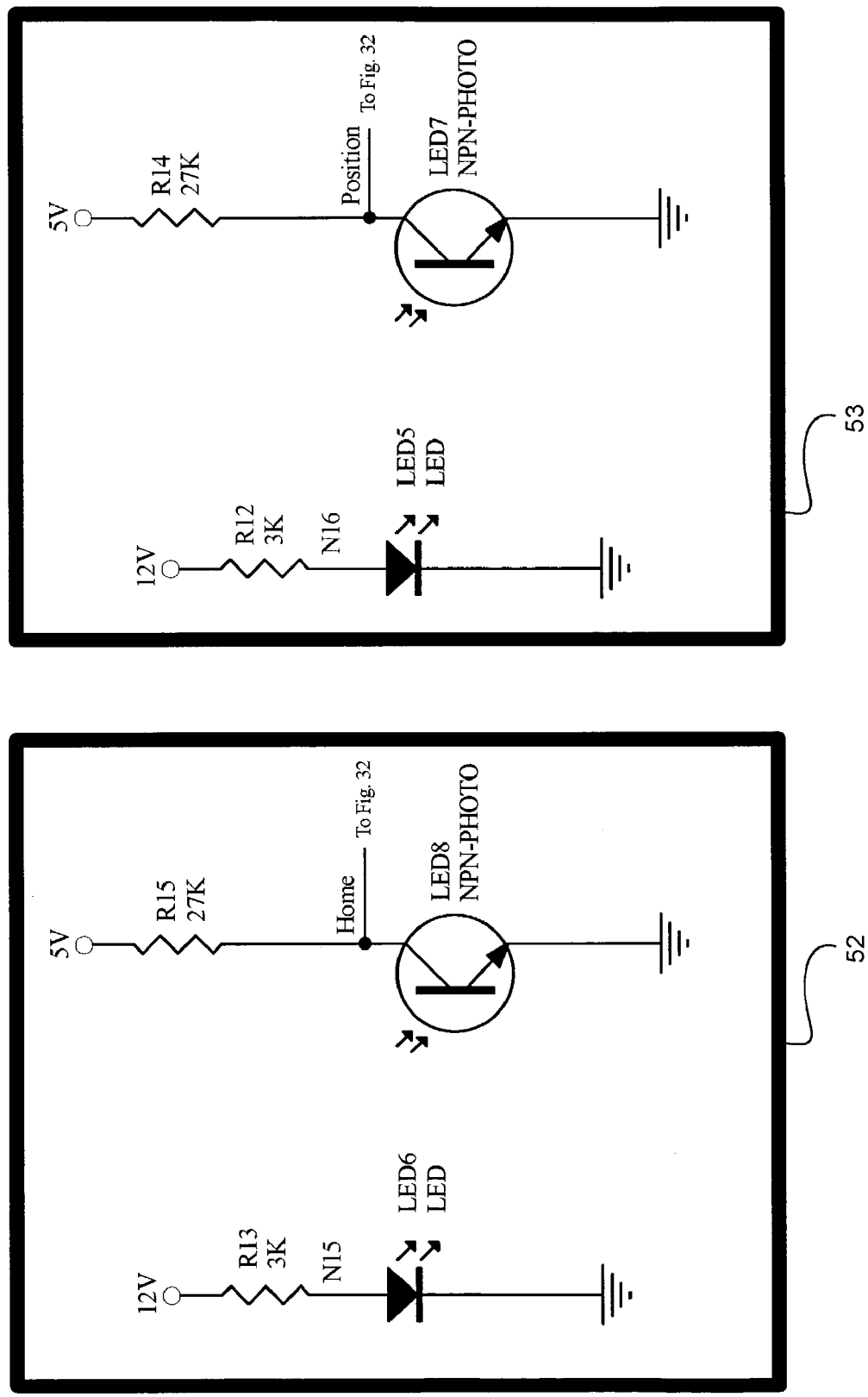
FIG. 33 is a schematic diagrams of the optical sensors.

Referring now to FIGS. 8, 14, 17, and 27, a second preferred embodiment of the positioning assembly 72 generally includes first and second optical sensors 52, 53 and first and second rings 54, 55. The first and second optical sensors 52, 53 are preferably mounted at points 98, 100 on the main printed circuit board assembly 32 as shown in FIG. 14. The main printed circuit board assembly 32 can be mounted between the platter 19 and the cartridge-receiving cavity 47 formed in the top housing 2 as shown in FIGS. 14 and 2. The optical sensors 52, 53 are preferably slot optical switches and can be configured schematically as shown in FIG. 33. A suitable commercially available slot optical switch for both the first and second optical sensors 52, 53 is the ITR8402-A/F3 slot optical switch manufactured by Everlight Electroniccs Co., Ltd. No 25, Lane 76, Chung Yang Rd, Sec. 3 Tucheng, Tapei 236, Taiwan, R.O.C.

Figure 19:
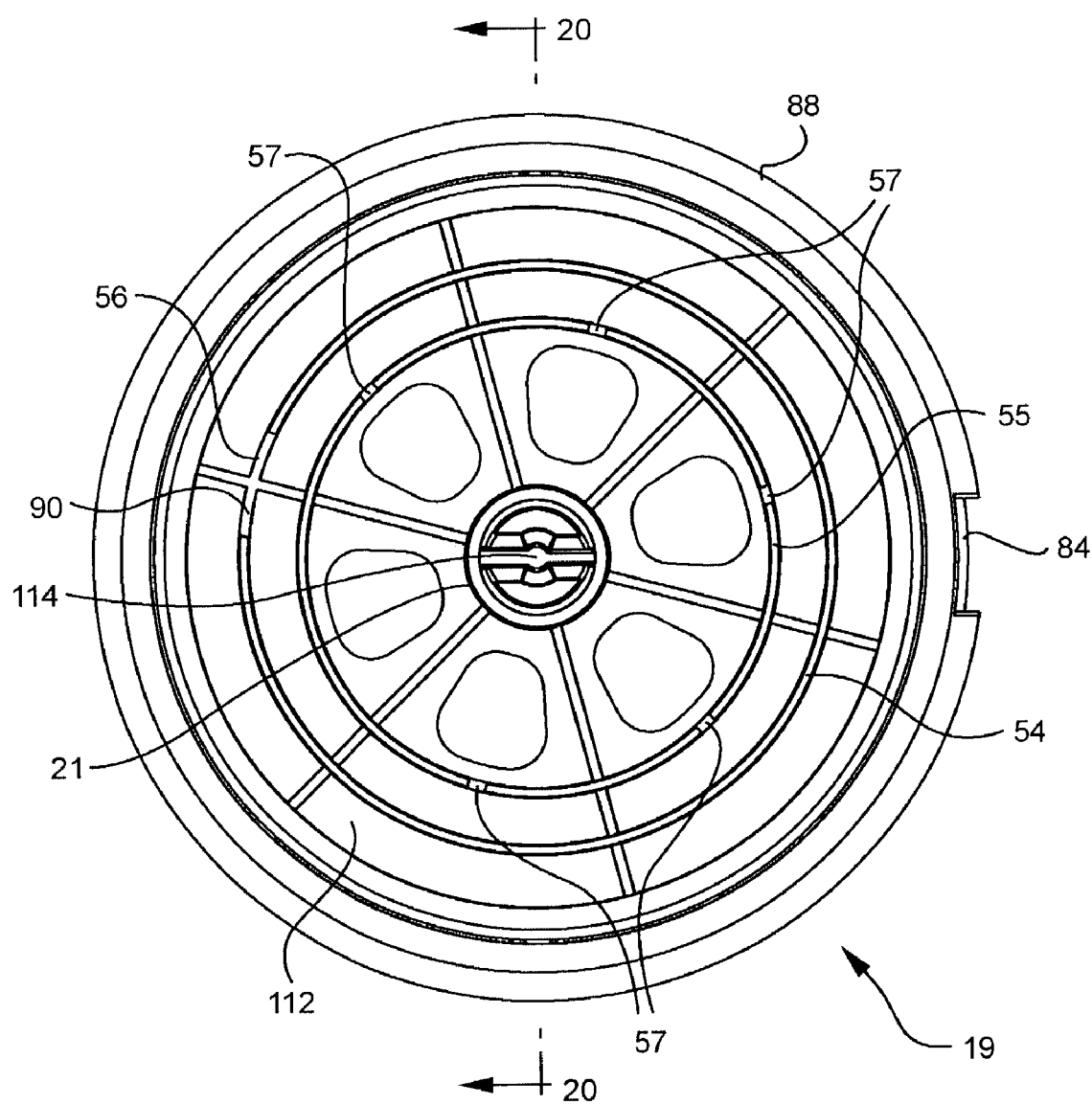
FIG. 19 is a top plan view of the platter.
Figure 20:
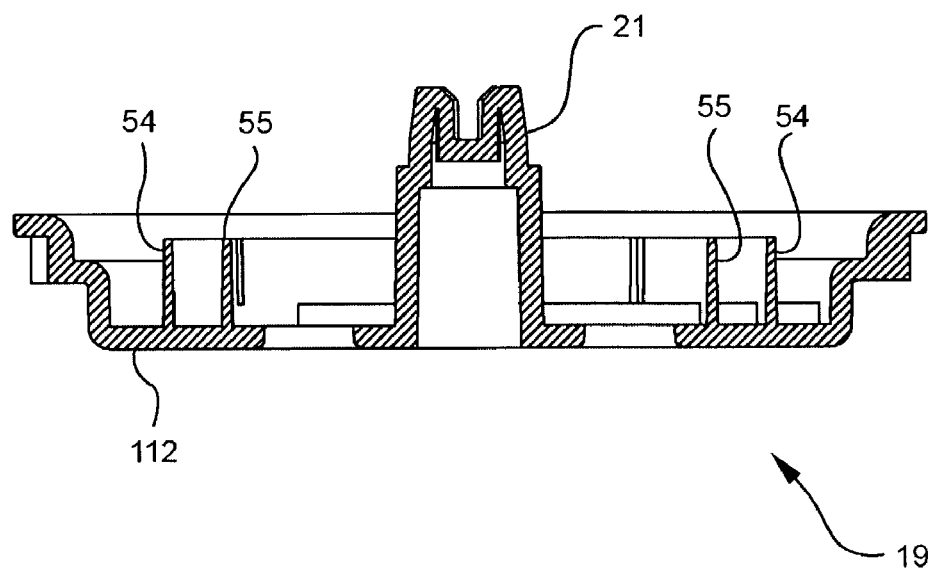
FIG. 20 is a cross-sectional view taken along line 20—20 on FIG. 19 of the platter.
Figure 21:
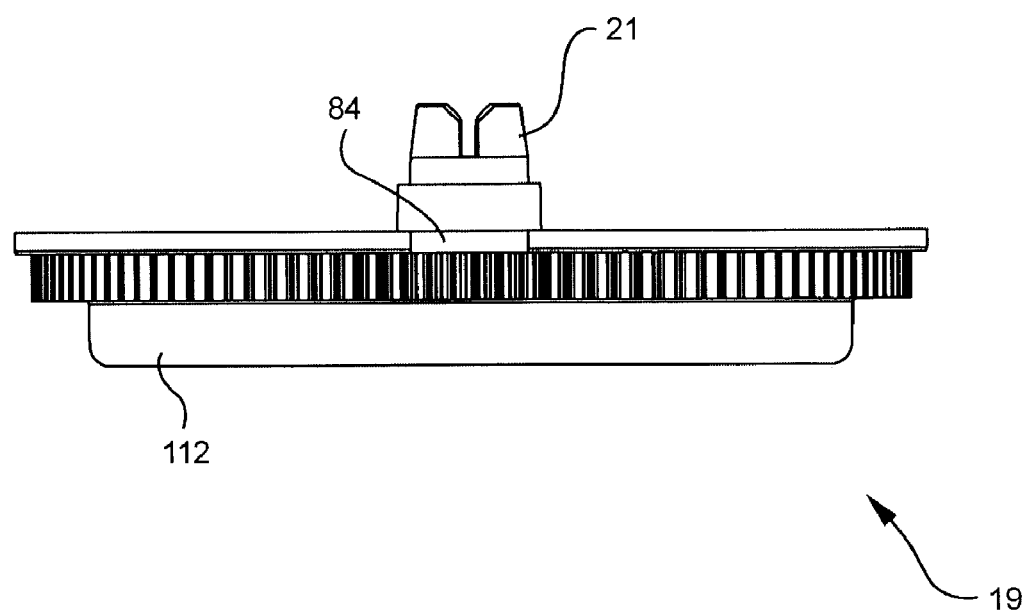
FIG. 21 is a side elevational view of the platter.

The first and second rings 54, 55 are preferably tubular and are mounted to the platter 19 about the axis of rotation defined by the hub 21 as shown in FIGS. 19 and 20. The first ring 54 is formed with a home notch 56 which generally corresponds to a starting and stopping position for the disk within the cartridge 42 generally referred to as the home position. The second ring 55 is formed with a plurality of position notches 57. Each of the position notches 57 generally corresponds to the location of a scent element on the disk within the cartridge 42.

Figure 28:
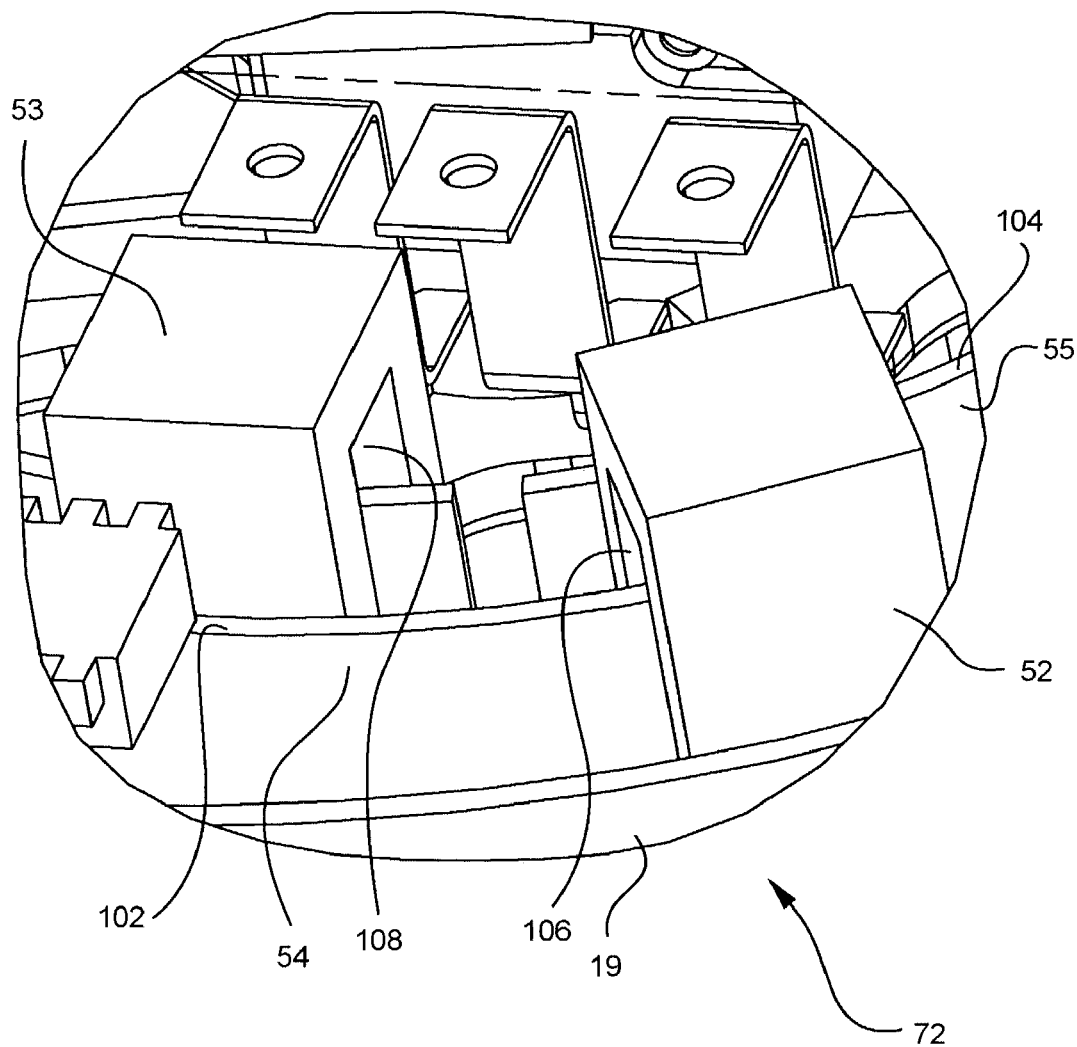
FIG. 28 is an enlarged detail showing the relationship between main printed circuit board and the platter.
Figure 29:
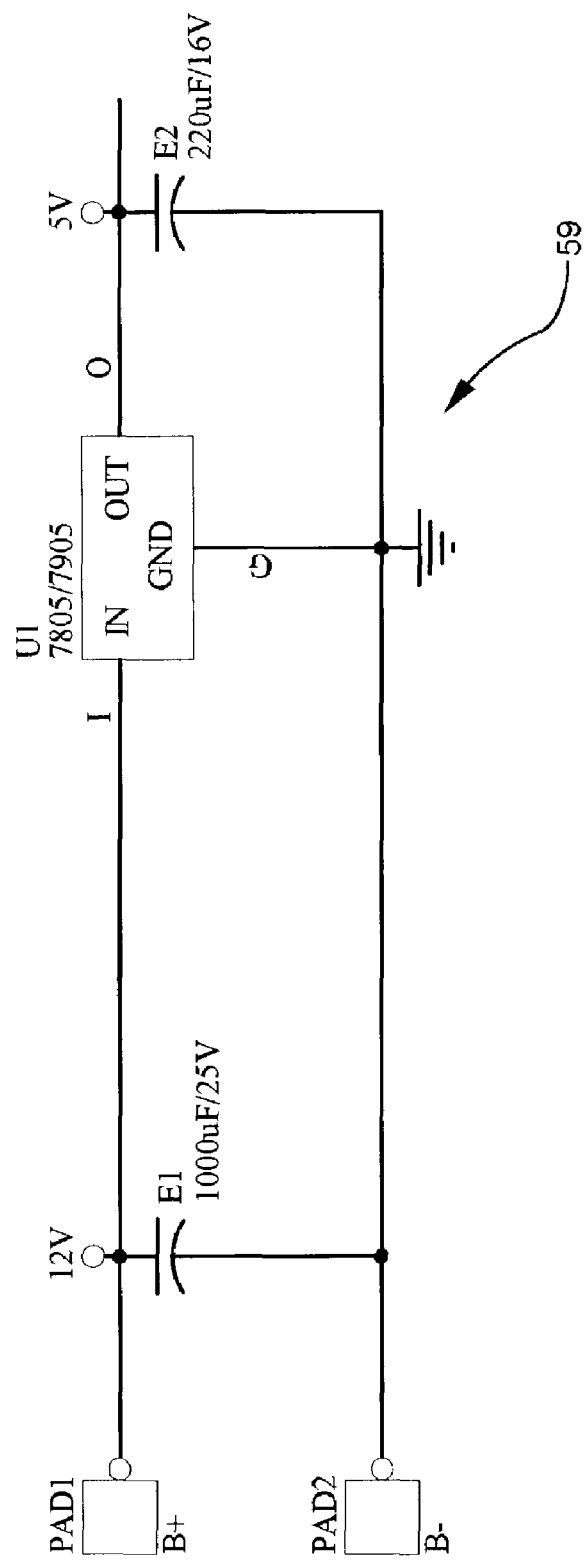
FIG. 29 is a schematic diagram of a power supply circuit.

Referring now to FIGS. 26, 27, and 28, the first and second optical sensors 52, 53 are arranged on the main printed circuit board assembly 32 so that an edge 102, 104 of each of the first and second rings 54, 55 rides within the slot 106, 108 formed in each respective sensor 52, 53. When the drive assembly 66 is operating to rotate the platter 19, the notches 56, 57 on both the first and second rings 54, 55 are rotated through circular paths 92, 94. The first optical sensor 52 will detect the presence of the home notch 56 and send a signal to a control unit 73. Similarly, the second optical sensor 53 will detect the presence of the position notches 57 and will send a signal to the control unit 73. As discussed further below, the control unit 73 generally will stop the drive assembly 66 when the second optical sensor 53 detects one of the position notches 57 to play the scent element associated with that location. The device 43 includes the first optical sensor 52 and the first ring 54 formed with the home notch 56 to provide a signal to the control unit 73 that the disk is at the home position. The control unit 73 is configured to track the playing of the scent elements associated with the position notches 57 on the second ring 55.

In another alternative embodiment (not shown), the position indicators could be permanent magnets and the sensors could be magnetic sensors configured to detect the presence of the permanent magnets. The magnets would be located at positions corresponding to the location of the notches as shown in FIG. 19.

Referring initially to FIG. 26, the control unit 73 generally includes a main printed circuit board 32, an intensity printed circuit board 33 and a play-skip printed circuit board 34. The control unit 73 is shown schematically in FIGS. 29 through 33.

Figure 5:
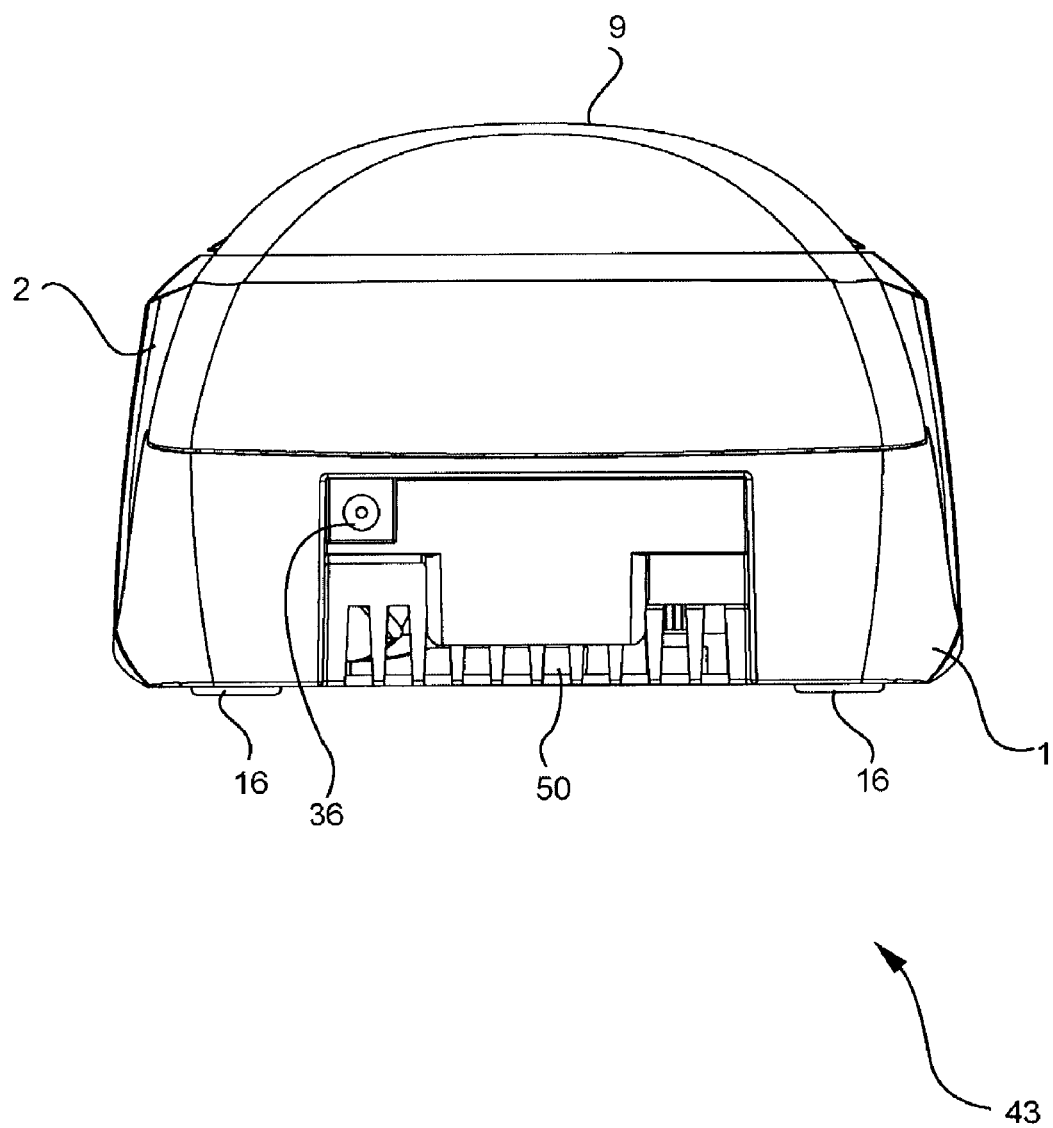
FIG. 5 is a rear elevational view of the present invention.
Figure 6:
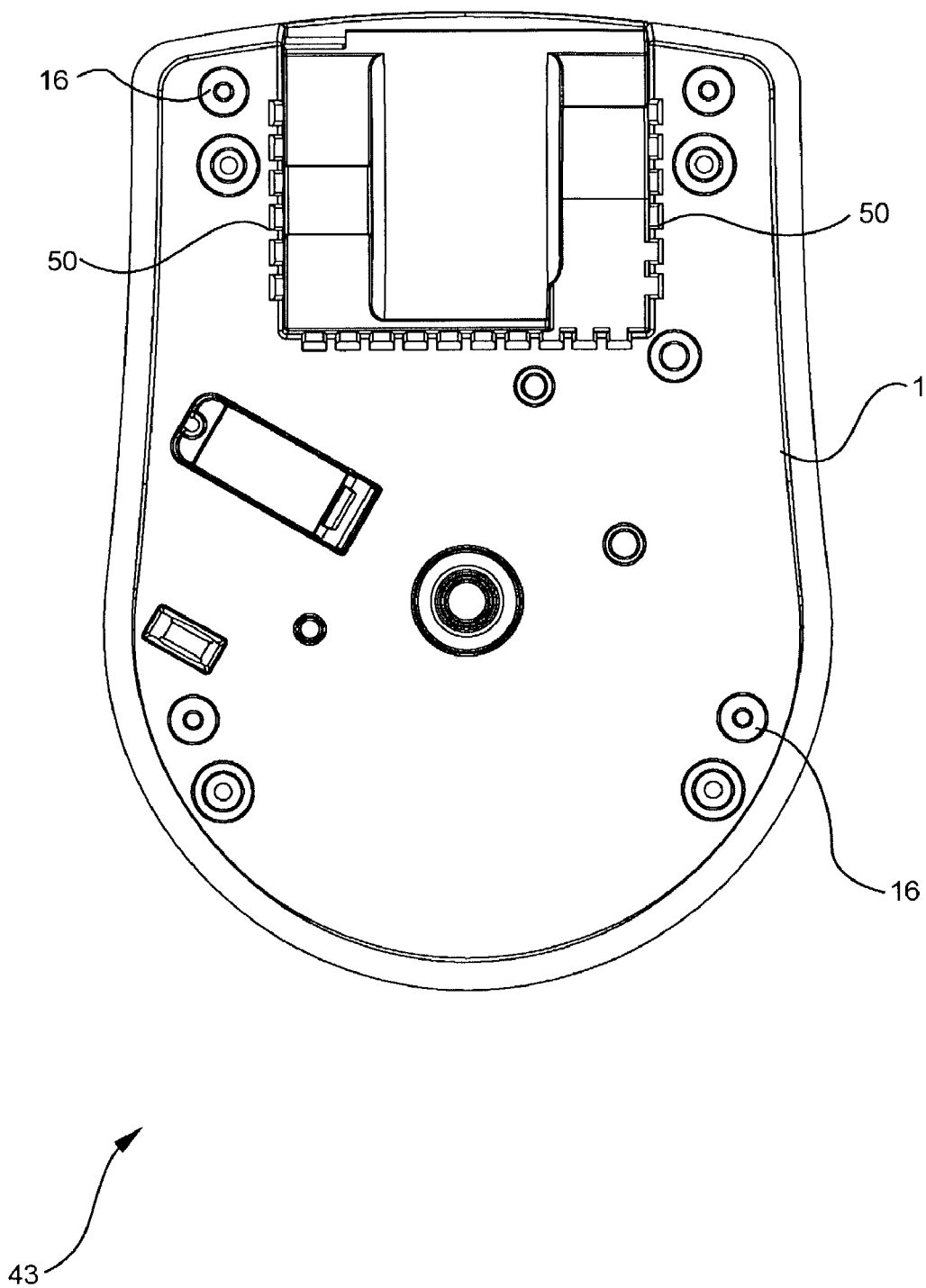
FIG. 6 is a bottom plan view of the present invention.

A schematic diagram of a power supply circuit 59 is shown in FIG. 24 where a 12V dc power source is preferably provided across pad1 and pad2, with the positive terminal of the 12V power source being provided on pad1 and ground being provided on pad2. The jack 36 shown in FIG. 5 is preferably electrically connected to pad1 and pad2. An input terminal of a 12v-to-5v dc regulator 7805/7905 U1, which is commercially available from STMicroelectronics, 16350 West Bernardo Dr, San Diego—Rancho Bernardo, Calif. 92127, is preferably connected to pad1 and an output terminal of the regulator U1 preferably provides a 5V dc power source or Vcc. Bypass capacitors (1000 uF/25v) E1 and (220 uF/16v) E2 are preferably connected in parallel across the 12V and 5V power sources, respectively.

Referring now to FIG. 32, an eight-bit microcontroller EM78P153S U2, which is commercially available from Elan Microelectronics Corp., Ltd., No. 12, Innovation 1 st. Rd,. Science-Based Industrial Park, Hsinchu City, Taiwan, having one-time-programmable (OTP) read only memory (ROM) is preferably provided to control the operation of the control unit 73 in accordance with software stored in the OTP ROM.

The series connection of a light emitting diode LED 1, resistor R5, and switch SW1 is preferably connected across the 5v power source and a bias signal provided by the microprocessor U2. A node between the resistor R5 and the switch SW1 is connected to pin 2 of the microprocessor U2. The LED1 preferably provides an indication of a high setting for the device 43.

The series connection of a light emitting diode LED3, resistor R6, and switch SW2 is preferably connected across the 5v power source and the bias signal provided by the microprocessor U2. A node between the resistor R6 and the switch SW2 is connected to pin 3 of the microprocessor U2. The LED3 preferably provides an indication of a medium setting for the device 43.

The series connection of a light emitting diode LED2, resistor R7, and switch SW3 is preferably connected across the 5v power source and the bias signal provided by the microprocessor U2. A node between the resistor R7 and the switch SW1 is connected to pin 5 of the microprocessor U2. The LED2 preferably provides an indication of a low setting for the device 43.

The series connection of a light emitting diode LED4, resistor R8, and switch SW4 is preferably connected across the 5v power source and the bias signal provided by the microprocessor U2. A node between the resistor R8 and the switch SW4 is connected to pin 6 of the microprocessor U2. The LED4 preferably provides an indication that power has been applied to the device 43.

The microcontroller U2, LED1–LED4, and switches SW1–SW4 preferably incorporate two modes of operation. In a display mode, the bias signal is preferably input to the microcontroller U2. Pins 2, 3, 5, and 6 of the microcontroller U2 are used as outputs and selectively brought to a low level to energize the corresponding LED. In a select mode, the bias signal is preferably used as an output from the microcontroller U2 and the state of the switches SW1–SW4 are read on the corresponding pins 2, 3, 5, and 6 of the microcontroller U2.

A schematic diagram of the first optical sensor 52 and the second optical sensor 53 is shown in FIG. 33. The first optical sensor 52 preferably includes a 3 k ohm resistor R13 and a light emitting diode LED6 electrically coupled in series between the 12v power source and ground, as well as a photodetector LED8 and a 27 k ohm resistor R15 electrically coupled in series between the 5v power source and ground. A node between the resistor R15 and the photodetector LED8 is preferably connected to a home signal on pin 7 of the microcontroller U2 shown in FIG. 32.

When the light beam between LED6 and the photodetector LED8 is interrupted, the photodetector is preferably an open circuit and the microcontroller senses a high level (5v) on the home signal. Conversely, when the light beam between the LED6 and the photodetector LED8 is not interrupted, the photodetector is preferably a short circuit between the resistor R15 and ground and the microcontroller senses a low level (~0v) on the home signal.

Similarly, the second optical sensor 53 preferably includes a 3 k ohm resistor R12 and a light emitting diode LED5 electrically coupled in series between the 12v power source and ground, as well as a photodetector LED7 and a 27 k ohm resistor R14 electrically coupled in series between the 5v power source and ground. A node between the resistor R14 and the photodetector LED7 is preferably connected to a position signal on pin 7 of the microcontroller U2 shown in FIG. 32.

When the light beam between LED5 and the photodetector LED7 is interrupted, the photodetector is preferably an open circuit and the microcontroller senses a high level (5v) on the position signal. Conversely, when the light beam between the LED5 and the photodector LED7 is not interrupted, the photodetector is preferably a short circuit between the resistor R14 and ground and the microcontroller senses a low level (~0v) on the position signal.

Figure 30:
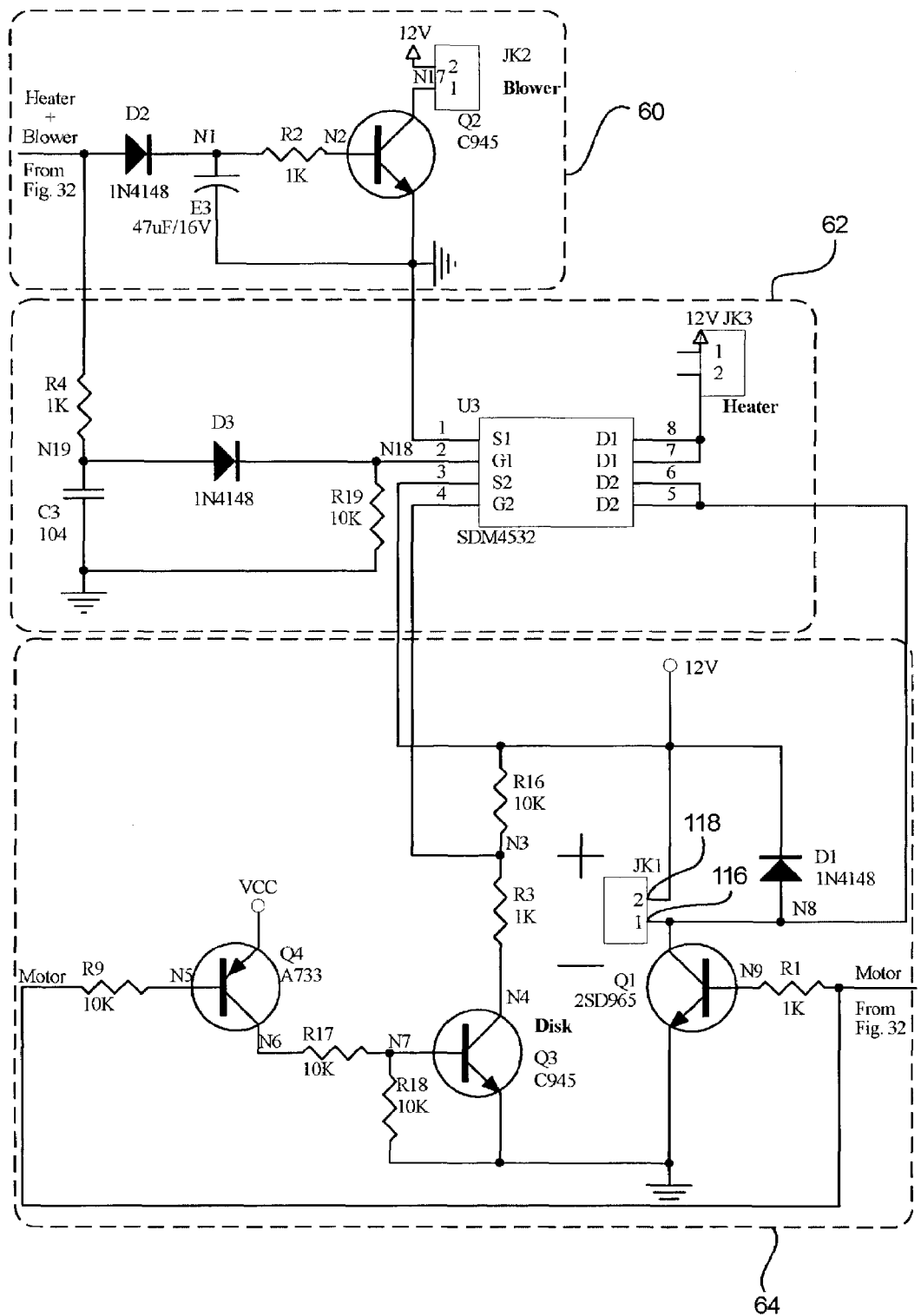
FIG. 30 is a schematic diagram of the blower, heater and motor circuits.

Referring now to FIG. 30, a blower circuit 60 preferably includes a C945 transistor Q2 and a blower connector JK2 coupled to a collector of the transistor Q2. The remaining terminal of the blower connector JK2 is preferably connected to the 12v power source. The blower connector JK2 enables the blower motor 35B (not shown) to be readily coupled thereto.

The combination of a diode 1N4148 D2 and a 1 k ohm resistor R2 are preferably connected in series between a heater+blower signal from pin 1 of the processor U2 and a base of the transistor Q2. A 47 uF/16v electrolytic capacitor E3 is preferably connected between a node N1, which is located between the diode D2 and the resistor R2, and ground. The collector of the transistor Q2 is preferably also connected to ground.

When the heater+blower signal from the processor U2 is high, the transistor Q2 is preferably driven to an on state, which essentially grounds one terminal of the blower connector JK2 and permits current to flow through the motor 35B of the blower assembly 70. Conversely, when the heater+blower signal from the processor U2 is low and the charge stored in capacitor E3 is insufficient to maintain transistor Q2 in the on state, the transistor Q2 is preferably driven to an off state, which essentially isolates one terminal of the blower connector JK2 and stops current from flowing through the motor 35B.

The blower assembly 70 is preferably controlled during a pulse mode by applying a positive pulse to the heater+blower signal. The positive pulse is sufficient to charge the capacitor E3, which maintains transistor Q2 in the on state and keeps the motor 35B on. However, the positive pulse is preferably insufficient to activate an NMOSFET U3, which turns the heating element 45 on, as described in greater detail below.

Referring again to FIG. 30, a heater circuit 62 preferably includes a heater connecter JK3, which is coupled to a heating element 45 (not shown in FIG. 30). One terminal of the heater connector JK3 is preferably connected to the 12v power source and the remaining terminal is preferably coupled to the drain of an enhancement mode n-channel field effect transistor NMOSFET U3, which is commercially available within a package of two devices as Part No. SDM4532 from Angus Technology Limited Workshop B, 7/F., Capital Trade Centre, No. 62, Tsun Yip Street, Kwun Tong, Kowloon, Hong Kong, China. The source of the NMOSFET U3 is preferably connected to ground.

The combination of a 1 k ohm resistor R4 and a 1N4148 diode D3 is preferably coupled in series between the heater+blower signal from the processor U2 and a gate of the NMOSFET U3. A capacitor C3 is preferably connected between a node N19, which separates the resistor R4 and the diode D3, and ground. A 10 k ohm resistor R19 is preferably connected between the gate of the NMOSFET U3 and ground.

When the heater+blower signal from the processor U2 is high, the NMOSFET U3 is preferably driven to an on state, which essentially grounds one terminal of the heater connector JK3 and permits current to flow through the heating element 45. Conversely, when the heater+blower signal from the processor U2 is low, the NMOSFET U3 is preferably driven to an off state, which essentially isolates one terminal of the heater connector JK3 and stops current from flowing through the heating element 45.

The heating element 45 is preferably controlled during a level mode by applying a dc level to the heater+fan signal. The dc level is sufficient to maintain transistor Q2 in the on state and keep the blower assembly 70 on, as well as turning the NMOSFET U3 on to keep the heating element 45 on. Thus, when the dc level is being applied during the level mode, both the blower assembly 70 and heating element 45 are on.

Referring again to FIG. 30, a motor circuit 64 preferably includes a motor connector JK1, which is coupled to the motor 35A (not shown in FIG. 30). One terminal of the motor connector JK1 is preferably connected to the 12v power source and the remaining terminal of the motor connector JK1 is preferably connected to a collector of a 2SD965 transistor Q1. The base of the transistor Q1 is preferably connected to a motor signal from pin 14 of the processor U2 through a 1 k ohm resistor R1 and the emitter of the transistor Q2 is preferably connected to ground. The collector of the transistor Q1 is preferably connected to a source of an enhancement mode p-channel field effect transistor PMOSFET U3 through a 1N4148 diode D1, as well as being connected to a drain of the PMOSFET U3.

The motor circuit 64 also includes a C945 transistor Q3, the collector of which is preferably connected to the source of the PMOSFET U3 through the series combination of a 10 k ohm resistor R16 and a 1 k ohm resistor R3. A node N3 separating the resistors R16 and R3 is preferably connected to a gate of the PMOSFET U3, and the emitter of the transistor Q3 is preferably connected to ground.

The base of the transistor Q3 is preferably coupled to ground through a 10 k ohm resistor R18 and is preferably coupled to the collector of an A733 transistor Q4 through a 10 k ohm resistor R17. The base of the transistor Q4 is preferably connected to the motor signal from pin 14 of the processor U2 through a 10 k ohm resistor R9, and the emitter of the transistor Q4 is preferably coupled to the 5v power source.

When the motor signal from the processor U2 is high, the transistor Q1 is preferably driven on, which essentially grounds a first terminal 116 of the motor connector JK1 and permits current to flow through the motor 35A. In addition, when the motor signal is high, the transistor Q4 is off and the transistor Q3 is off. This open circuits the current path from the 12V power source through resistors R16, R3 and transistor Q3, which enables the maximum amount of current flow through the motor 35A. Also, when transistor Q3 is off, the PMOSFET U3 is off, which isolates the first and second 116, 118 terminals of the motor 35A across the PMOSFET U3.

Conversely, when the motor signal from the processor U2 is low, the transistor Q1 is preferably off, which essentially isolates the first terminal 116 of the motor connector JK1 from ground, which stops current from flowing through the motor 35A. In addition, when the motor signal is low, the transistor Q4 is preferably driven on, which drives the transistor Q3 on. This provides a current path from the 12V power source through resistors R16, R3 and transistor Q3, which further diverts current flow from the motor 35A.

Also, when transistor Q3 is on, the PMOSFET U3 is driven on, which short circuits the first and second terminals 116, 118 of the motor 35A through the PMOSFET U3 to ensure that there is substantially no voltage drop between the first and second motor terminals 116, 118. Thus, the motor circuit 64 formed in accordance with the present invention provides at least three mechanisms that stop the rotation of the motor 35A in response to the motor signal from the processor U2 as rapidly as possible. Referring again to FIG. 30, the following Table illustrates the approximate voltage and resistance values associated with positions shown on FIG. 30 while the motor 35A is either running or stopped:

| Table of Voltage and Resistance values at run and stop position of Motor 35A | | |
| --- | --- | --- |
| Position shown in FIG. 30 | Run | Stop |
| motor signal voltage | 5 V | 0 V |
| MOSFET impedance | high Z | short |
| N3 voltage | 12 V | 1.07 V |
| N6 voltage | 0 V | 12 V |
| N7 voltage | 0 V | 0.7 V |
| N8 voltage | 0 V | 12 V |
| N9 voltage | 0.7 V | 0 V |

Figure 31:
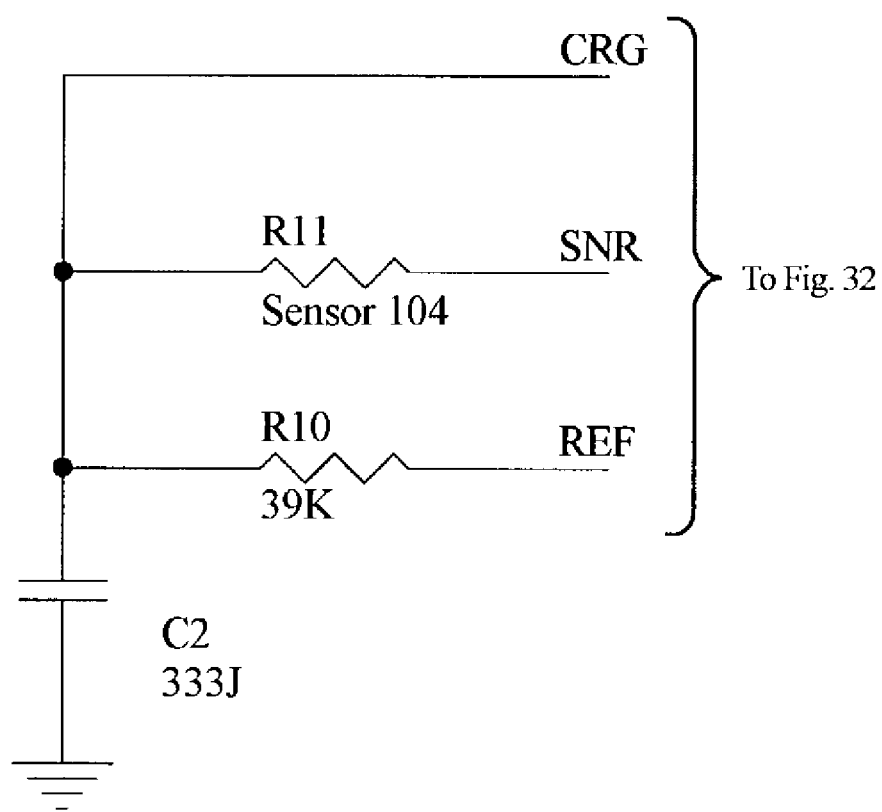
FIG. 31 is a schematic diagram of a circuit.

FIG. 31 shows a thermistor R11 preferably coupled in series with a capacitor C2 between an SNR signal on pin 8 of the microcontroller U2 and ground. The thermistor R11 exhibits a determinable change in resistance due to changes in temperature, and thus the microcontroller U2 preferably uses the SNR signal as an input to monitor the temperature in the vicinity of the heating element 45.

A resistor R10 is preferably coupled in series with the capacitor C2 between a REF signal on pin 9 of the microcontroller U2 and ground. The microcontroller U2 preferably uses the REF signal as a reference for comparison with the SNR signal to cancel the effect of ambient temperature fluctuations. The microcontroller U2 preferably charges the capacitor C2 through a CRG signal, which couples pin 10 of the microcontroller U2 to the capacitor C2. The microcontroller U2 then monitors the width of the pulse on the SNR signal, which is dependent on the resistance of the thermistor R11, to determine the temperature in the vicinity of the heating element 45.

The operation of the device 43 will now be explained with reference to the drawings to further describe the present invention. A user will generally first provide power to the device 43 by plugging a 12V DC power pack into an outlet and connect the device to the 12V power supply through jack 36 shown in FIG. 5. The user will next insert a cartridge 42 into the cartridge-receiving cavity 47 and close the top cover 7. The control unit 73 will now receive power because the cartridge 42 will depress the electrical switch 78 (SW1 on FIG. 32) located in the cartridge-receiving cavity 47. The latch 31 will engage a lip 82 located on the lower portion 8 of the top cover 7 to initially maintain the device 43 in a closed position while the disk within the cartridge 42 and the platter 19 are located at the home position.

The user will next press the play button 13 on the right control panel 11 to start both the drive assembly 66 and the blower assembly 70. Once the platter 19 is rotated from the home position, the top cover 7 will be locked in the closed position until the platter 19 returns to the home position. Preferably LED4 on the play-skip printed circuit board 34 will blink as the disk is rotating to locate the first scent element over the heater assembly 68 to alert the user that the disk is being rotated. After the first scent element is located over the heating assembly 68, the heating element 45 will turn on, and preferably LED4 will go from a blinking state to a steady on state. The heating element 45 will generally turn on to a default setting for the intensity level, which can generally include low, medium, or high. The intensity level is preferably displayed on the left control panel 10, which can be selected by pressing button 12. The control unit 73 can be configured to remember the last intensity level selected by the user for playing a cartridge 42. Preferably the control unit 73 monitors the temperature of the heating element 45 and pulses the current to the heating element 45 to maintain the desired intensity level. The temperature can generally be monitored using a thermistor R11 as shown on FIG. 31.

A scent element in the cartridge 42 is generally played for a play period selected to be long enough for the user to comprehend and appreciate an aroma while not exceeding an interval of time in which the user would become desensitized to the aroma, which is sometimes referred to as "fragrance fatigue" or "habituation." See U.S. Patent Application Publication No.: US 2002/0068010 A1. The play period can be in a range from about 15 to 60 minutes, and is preferably about 30 minutes. The play period is also generally related to both a time for activating the scent element and a time for diffusing the activated scent element. Where the activation is performed by heating the scent element, it has been found that activation is generally not required through the entire play period in which the activated scent element will be diffused. Accordingly, it is preferable to activate the scent element for a shorter period than the play period selected for diffusing the activated scent element. The shorter period can be in a range from about 5 to 10 minutes, and is preferably about 8 minutes. For example, when the play period for diffusing an activated scent element is selected to be about 30 minutes, a suitable period for activating the element has been found to be about 22 minutes. This is beneficial in that it allows the scent element to cool for about 8 minutes before rotating the disk within the cartridge 42.

After the play period for diffusing the activated scent element (generally about 30 minutes) has expired, the control unit 73 will preferably rotate the disk to position the next scent element over the heating assembly 68. Again, preferably LED4 on the play-skip printed circuit board 34 will blink as the disk is being rotated. This process will generally repeat itself until the last scent element is played. After the last scent element is played, the control unit 73 will continue to operate the blower assembly 70 while monitoring the temperature. The device 43 will finally rotate the disk into the home position after the temperature falls below 70 C.

When a user decides to stop playing a cartridge before all of the scent elements are played, the user can press the play button 13 again. The electronic controls will turn the heating assembly 68 off, and preferably make LED4 blink again. The control unit 73 will also continue to operate the blower assembly 70 while monitoring the temperature. Once the temperature falls below 70 C, the device 43 will rotate the disk into the home position and turn off the blower assembly 70 and LED4.

When a user decides to skip a scent element, the user can press the skip button 14. The control unit 73 will generally turn the heating assembly 68 off, and preferably make LED4 blink again. The control unit 73 will also continue to operate the blower assembly 70 while rotating the disk to the next position. Once the next scent element arrives at a position over the heating assembly 68, the normal program will resume. However, if the skip button 14 is pressed when the device 43 is playing the last scent element, the control unit 73 will operate the device 43 in the same manner as though the user pressed the play button (stop button) 13 again as described above to stop the device 43.

If the device 43 loses power during operation, the control unit 73 is configured to return the disk to the home position after power is restored. In addition, the device 43 will go into a standby mode where the unit has power.

Although illustrative embodiments of the present invention have been described herein with reference to the accompanying drawings, it is to be understood that the invention is not limited to those precise embodiments, and that various other changes and modifications may be effected by one skilled in the art without departing from the scope or spirit of the invention.

What is claimed is:

1. An apparatus for rotating a disk having a plurality of scent elements supported thereon, the apparatus comprising;
   a platter having a hub extending upwardly from a center thereof, said hub configured to removably engage the disk in a predetermined rotational position and defining an axis of rotation;
   a motor coupled to said platter for rotating said platter about said axis of rotation;
   a first position indicator disposed on said platter to rotate about said axis of rotation through a first circular path, wherein said first position indicator comprises at least one notch formed on a ring extending upwardly from said platter and concentric with said hub;
   a first sensor arranged adjacent to a first point on said first circular path and generating a signal when said first position indicator is rotated to said first point; and
   a control unit coupled to said first sensor and said motor, said control unit controlling current delivered to said motor to operate said motor and altering the current upon receiving said signal from said first sensor.

2. An apparatus for rotating a disk as defined by claim 1, wherein said first sensor is an optical sensor configured to detect said at least one notch.

3. An apparatus for rotating a disk as defined by claim 2, wherein said ring includes an edge and said optical sensor is formed with a slot for said edge to ride within.

4. An apparatus for rotating a disk having a plurality of scent elements supported thereon, the apparatus comprising:
   a platter having a hub extending upwardly therefrom, said hub configured to removably engage the disk in a predetermined rotational position and defining an axis of rotation;
   a motor coupled to said platter for rotating said platter about said axis of rotation;
   a first ring disposed on said platter concentric with said hub, said first ring having at least one notch formed therein to rotate about said axis of rotation through a first circular path;
   a second ring disposed on said platter concentric with said first ring, said second ring having a plurality of notches formed therein to rotate about said axis of rotation through a second circular path;
   a first sensor arranged adjacent to a first point on said first circular path and generating a first signal when said notch of said first ring is rotated to said first point;
   a second sensor arranged adjacent to a second point on said second circular path and generating a second signal when a notch of said plurality of second ring notches is rotated to said second point; and
   a control unit coupled to said first sensor, said second sensor and said motor, said control unit controlling current delivered to said motor to operate said motor and altering said current upon receiving said first signal from said first sensor and said second signal from said second sensor.

5. An apparatus for rotating a disk as defined by claim 4, wherein said notch of said first ring is associated with a home location of the disk.

6. An apparatus for rotating a disk as defined by claim 5, wherein each notch of said second ring is associated with an intermediate location of the disk.

7. An apparatus for rotating a disk as defined by claim 6, wherein said first sensor is an optical sensor configured to detect said first ring notch and said second sensor is an optical sensor configured to detect said plurality of second ring notches.

8. An apparatus for rotating a disk as defined by claim 6, wherein said first and second sensors are each formed with a slot for each respective ring to ride within.

9. A device for playing a cartridge having a plurality of scent elements supported on a rotatable disk, said device comprising:
   a housing having a cavity for receiving the cartridge and being formed with an air intake and an exhaust port;
   a blower assembly mounted within said housing for generating an airflow by drawing air in through said air intake over said cavity and out through said exhaust port;
   a heater for healing a scent element when a cartridge is positioned within said cavity;
   a spring for biasing said heater toward the cartridge when the cartridge is positioned within said cavity;

a platter having a body defined by a perimeter and a center, a hub connected to said body at said center to define an axis of rotation generally perpendicular to said airflow generated by said blower and being configured to removably engage the rotatable disk of the cartridge in a predetermined rotational position, a first position indicator disposed on said body, and a second position indicator disposed on said body;

a motor mounted within said housing and coupled to said platter for rotating said platter about said axis of rotation so that said first position indicator rotates through a first circular path and said second position indicator rotates through a second circular path;

a first sensor for generating a first signal when said first position indicator is rotated to a first point;

a second sensor for generating a second signal when said second position indicator is rotated to a second point; and a control unit coupled to said first sensor, said second sensor and said motor, said control unit controlling current delivered to said motor in response to said first signal from said first sensor and said second signal from said second sensor.

10. A device for playing a cartridge as defined by claim 9, wherein said first position indicator comprises at least one notch formed on a first ring extending upwardly from said platter and concentric with said hub, said notch corresponding with a home position of the rotatable disk of the cartridge.

11. A device for playing a cartridge as defined by claim 10, wherein said second position indicator comprises at least one notch formed on a second ring extending upwardly from said platter and concentric with said first ring, said notch corresponding with a location of at least one of the plurality of scent elements on the rotatable disk of the cartridge.

12. A device for playing a cartridge as defined by claim 11, wherein said first sensor is an optical sensor configured to detect said notch corresponding to the home position of the rotatable disk of the cartridge and said second sensor is an optical sensor configured to detect said at least one notch corresponding with a location of at least one of the plurality of scent elements on the rotatable disk of the cartridge.

13. A device for playing a cartridge as defined by claim 12, wherein said first and second optical sensors are each formed with a slot for each respective ring to ride within.

14. A device for playing a cartridge as defined by claim 9, wherein said first and second position indicators are magnets and said first and second sensors are magnetic sensors configured to detect said respective magnet.

15. A device for playing a cartridge as defined by claim 11, wherein said control unit is configured to sequentially rotate said hub from the home location through each of the locations corresponding to one of the plurality of scent elements on the rotatable disk and back to the home location.

16. A device for playing a cartridge as defined by claim 15, wherein said control unit is configured to stop the rotation of said hub for a play period at each of the plurality of scent elements.

17. A device for playing a cartridge as defined by claim 9, further comprising:

a cover being hingedly connected to said housing for covering said cavity when in a closed position;

a latch configured to maintain said cover in said closed position and being formed with a key; and wherein said perimeter of said platter is formed with a latch notch associated with a home location and configured to receive said key so that said latch can be translated to open said cover when said platter is at said home location.

18. An apparatus for rotating a disk as defined in claim 1, wherein said platter hub includes a groove extending perpendicularly to said axis of rotation.

19. An apparatus for rotating a disk as defined in claim 1, wherein said platter further includes a latch notch formed on a perimeter edge thereof; said latch notch being configured to release a latch when said platter is rotated to a home position.

20. An apparatus for rotating a disk as defined in claim 1, further comprising a heater disposed adjacent said platter and a spring for biasing said heater.

21. An apparatus for rotating a disk as defined in claim 4, wherein said platter hub includes a groove extending perpendicularly to said axis of rotation.

22. An apparatus for rotating a disk as defined in claim 4, wherein said platter further includes a latch notch formed on a perimeter edge thereof, said latch notch being configured to release a latch when said platter is rotated to a home position.

23. An apparatus for rotating a disk as defined in claim 4, further comprising a heater disposed adjacent said platter and a spring for biasing said heater.

24. A device for playing a cartridge as defined in claim 9, wherein said platter hub includes a groove extending perpendicularly to said axis of rotation.

* * * * *